(12) United States Patent
Olson

(10) Patent No.: US 10,111,723 B2
(45) Date of Patent: Oct. 30, 2018

(54) SYSTEM AND METHOD FOR DETECTION AND AVOIDANCE OF COLLISION OF ROBOTICALLY-CONTROLLED MEDICAL DEVICES

(71) Applicant: St. Jude Medical, Atrial Fibrillation Division, Inc., St. Paul, MN (US)

(72) Inventor: Eric S. Olson, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 189 days.

(21) Appl. No.: 15/148,078

(22) Filed: May 6, 2016

(65) Prior Publication Data

US 2016/0324587 A1   Nov. 10, 2016

Related U.S. Application Data

(63) Continuation of application No. 14/368,989, filed as application No. PCT/US2012/030697 on Mar. 27, 2012, now Pat. No. 9,333,044.

(60) Provisional application No. 61/581,838, filed on Dec. 30, 2011.

(51) Int. Cl.
*A61B 34/00* (2016.01)
*A61B 34/37* (2016.01)
(Continued)

(52) U.S. Cl.
CPC .............. *A61B 34/37* (2016.02); *A61B 34/20* (2016.02); *A61B 34/30* (2016.02); *A61B 34/32* (2016.02);
(Continued)

(58) Field of Classification Search
CPC ......... A61B 34/20; A61B 34/30; A61B 34/37; A61B 34/32; A61B 2034/102;
(Continued)

(56) References Cited

U.S. PATENT DOCUMENTS

| 4,578,757 A | 3/1986 | Stark |
|---|---|---|
| 6,142,993 A | 11/2000 | Whayne |

(Continued)

FOREIGN PATENT DOCUMENTS

EP   1901151   3/2008

OTHER PUBLICATIONS

An International Search Report for PCT Application No. PCT/US2012/030697, dated Jul. 17, 2012. 3 pgs.
(Continued)

*Primary Examiner* — Nicholas Kiswanto
(74) *Attorney, Agent, or Firm* — Dykema Gossett PLLC

(57) ABSTRACT

A robotic catheter control system includes a collision detection logic configured to determine a collision metric indicative of a collision between a medical device that is manipulated by the robotic control system and an object. The object may be an anatomical feature or can be another medical device, including another device being manipulated by the robotic control system. The collision detection logic produces virtual representations of the medical device and the object and uses these representation to determine collision. Geometrical solids, such as spheres, are used to represent the outer surfaces of the devices and the logic determines whether the respective surfaces intersect, thereby indicating collision. Collision avoidance involves estimating future device poses and then computing an alternate path computation so as avoid predicted collision(s).

19 Claims, 14 Drawing Sheets

(51) Int. Cl.
*A61B 34/30* (2016.01)
*A61B 34/32* (2016.01)
*A61B 34/20* (2016.01)
*G06F 19/00* (2018.01)
*A61B 34/10* (2016.01)
*A61M 25/01* (2006.01)

(52) U.S. Cl.
CPC .... *G06F 19/3418* (2013.01); *A61B 2034/102* (2016.02); *A61B 2034/105* (2016.02); *A61B 2034/107* (2016.02); *A61B 2034/301* (2016.02); *A61M 2025/0166* (2013.01); *F04C 2270/041* (2013.01); *Y10S 901/09* (2013.01)

(58) Field of Classification Search
CPC ........ A61B 2034/105; A61B 2034/107; A61B 2034/301; G06F 19/3418; A61M 2025/0166; F04C 2270/041; Y10S 901/09
See application file for complete search history.

(56) References Cited

U.S. PATENT DOCUMENTS

| | | |
|---|---|---|
| 6,696,844 B2 | 2/2004 | Wong |
| 7,769,429 B2 * | 8/2010 | Hu .................... A61B 5/103 |
| | | 600/424 |
| 7,773,792 B2 | 8/2010 | Kimmel |
| 8,005,659 B2 | 8/2011 | Nelson |
| 8,086,008 B2 | 12/2011 | Coste-Maniere et al. |
| 8,920,368 B2 * | 12/2014 | Sandhu ................. A61B 34/25 |
| | | 604/95.01 |
| 8,971,597 B2 | 3/2015 | Zhao et al. |
| 9,265,468 B2 * | 2/2016 | Rai ....................... A61B 6/463 |
| 2007/0167706 A1 | 7/2007 | Boese |
| 2008/0020362 A1 | 1/2008 | Cotin |
| 2008/0039746 A1 | 2/2008 | Hissong |
| 2009/0192524 A1 | 7/2009 | Itkowitz et al. |
| 2010/0256558 A1 | 10/2010 | Olson |
| 2011/0066282 A1 | 3/2011 | Bosscher et al. |
| 2011/0091853 A1 * | 4/2011 | Shachar ............... G09B 23/285 |
| | | 434/262 |
| 2011/0178532 A1 | 7/2011 | Amiri et al. |
| 2011/0218774 A1 | 9/2011 | Ikits |
| 2012/0172795 A1 | 7/2012 | Sandhu et al. |
| 2012/0211006 A1 | 8/2012 | Gill et al. |
| 2016/0128786 A1 * | 5/2016 | Weber .................... G06T 7/251 |
| | | 382/128 |

OTHER PUBLICATIONS

A Supplementary European Search Report for EP Application No. 12861682, dated Sep. 7, 2015. 1 pg.

* cited by examiner

SYSTEM AND METHOD FOR DETECTION AND AVOIDANCE OF COLLISION OF ROBOTICALLY-CONTROLLED MEDICAL DEVICES

CROSS-REFERENCE TO RELATED APPLICATIONS

This application is a continuation of U.S. application Ser. No. 14/368,989, filed 26 Jun. 2014, which is a national stage filing based upon international application no. PCT/US2012/030697, filed 27 Mar. 2012, which claims the benefit of U.S. provisional application No. 61/581,838 filed 30 Dec. 2011, all of which are hereby incorporated by reference in their entirety.

BACKGROUND OF THE INVENTION a. Field of the Invention

The present disclosure relates generally to a remote catheter guidance system (RCGS) for a plurality of medical devices, and more particularly to a collision detection and/or avoidance function for such an RCGS.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments.

In a typical EP procedure, a physician manipulates a catheter through a patient's vasculature to, for example, a patient's heart. The catheter typically carries one or more electrodes that may be used for mapping, ablation, diagnosis, and the like. Once at the target tissue site, the physician commences diagnostic and/or therapeutic procedures, for example, ablative procedures such as radio frequency (RF), microwave, cryogenic, laser, chemical, acoustic/ultrasound or high-intensity focused ultrasound (HIFU) ablation, to name a few different sources of ablation energy. The resulting lesion, if properly located and sufficiently contiguous with other lesions, disrupts undesirable electrical pathways and thereby limits or prevents stray electrical signals that can lead to arrhythmias. Such procedures require precise control of the catheter during navigation to and delivery of therapy to the target tissue site, which can invariably be a function of a user's skill level.

Robotic catheter systems are known to facilitate such precise control. Robotic catheter systems generally carry out (as a mechanical surrogate) input commands of a clinician or other end-user to deploy, navigate and manipulate a catheter and/or an introducer or sheath for a catheter or other elongate medical instrument, for example, a robotic catheter system disclosed in U.S. utility patent application Ser. No. 12/347,811, filed 31 Dec. 2008 and published 1 Oct. 2009 under publication no. US 2009/0247993 A1, now pending, which is hereby incorporated by reference in its entirety as though fully set forth herein. Despite these improvements, physicians and patients would benefit from even further enhancement in the capabilities provided by such an RCGS.

There is therefore a need for improved systems and methods that enhance physician control and provide improved functionality in performing robotically-driven cardiac catheter procedures.

BRIEF SUMMARY OF THE INVENTION

One advantage of the methods and apparatus described, depicted and claimed herein relates to the reliable, simultaneous use of multiple medical devices in the body of a patient without collision of the devices.

The disclosure is directed to an apparatus for use in a robotic control system of the type suitable for manipulating a medical device in a body of a patient. The apparatus includes an electronic control unit (ECU) and a memory coupled to the ECU. The apparatus also includes collision detection logic stored in the memory and which is configured to be executed by the ECU. The collision detection logic is configured to determine a collision metric indicative of a collision between the medical device and an object. The collision detection logic operates in accordance with a predetermined detection strategy and uses virtual representations of both the medical device and the object in generating the collision metric. In embodiments, the object can comprise another device (e.g., a catheter), which may also be manipulated by the control system, an anatomical structure within the body, a sheath or the like.

In an embodiment involving multiple medical devices, the virtual representations include respective splines that correspond to the curves of the medical devices, which are in turn computed from measured node locations (e.g., electrode locations in an impedance-based localization system embodiment). The virtual representations further include geometrical solids, such as spheres, whose surfaces represent the surfaces of the actual medical devices. The collision determination logic is further configured to assess whether the respective surfaces of the geometrical solids associated with the devices intersect. If so, then the logic generates a collision metric indicative of a collision.

In further embodiments, collision avoidance and alternate path determination features are also presented.

The foregoing and other aspects, features, details, utilities, and advantages of the present disclosure will be apparent from reading the following description and claims, and from reviewing the accompanying drawings.

DETAILED DESCRIPTION OF THE INVENTION

Before proceeding to a detailed description of the collision detection and avoidance system for a robotic catheter system, a brief overview (for context) of an exemplary remote catheter guidance system (RCGS) for manipulating a medical device will first be described. The description will detail in general how the RCGS can be used to control the translation, distal bending and virtual rotation of a catheter and surrounding sheath. In addition, since the capabilities of the RCGS can be extended to manipulate multiple medical devices, further features applicable to a multi-device environment will be described. For example, the RCGS can be configured to manipulate a cardiac mapping catheter, an ablation catheter, and perhaps an imaging catheter, such an intracardiac echocardiography (ICE) catheter. With an RCGS manipulating a plurality of medical devices, a device collision detection and avoidance function is an essential capability. Thus, after the description of the RCGS, a description of a system and method for collision detection and avoidance will be set forth.

Figure 1:
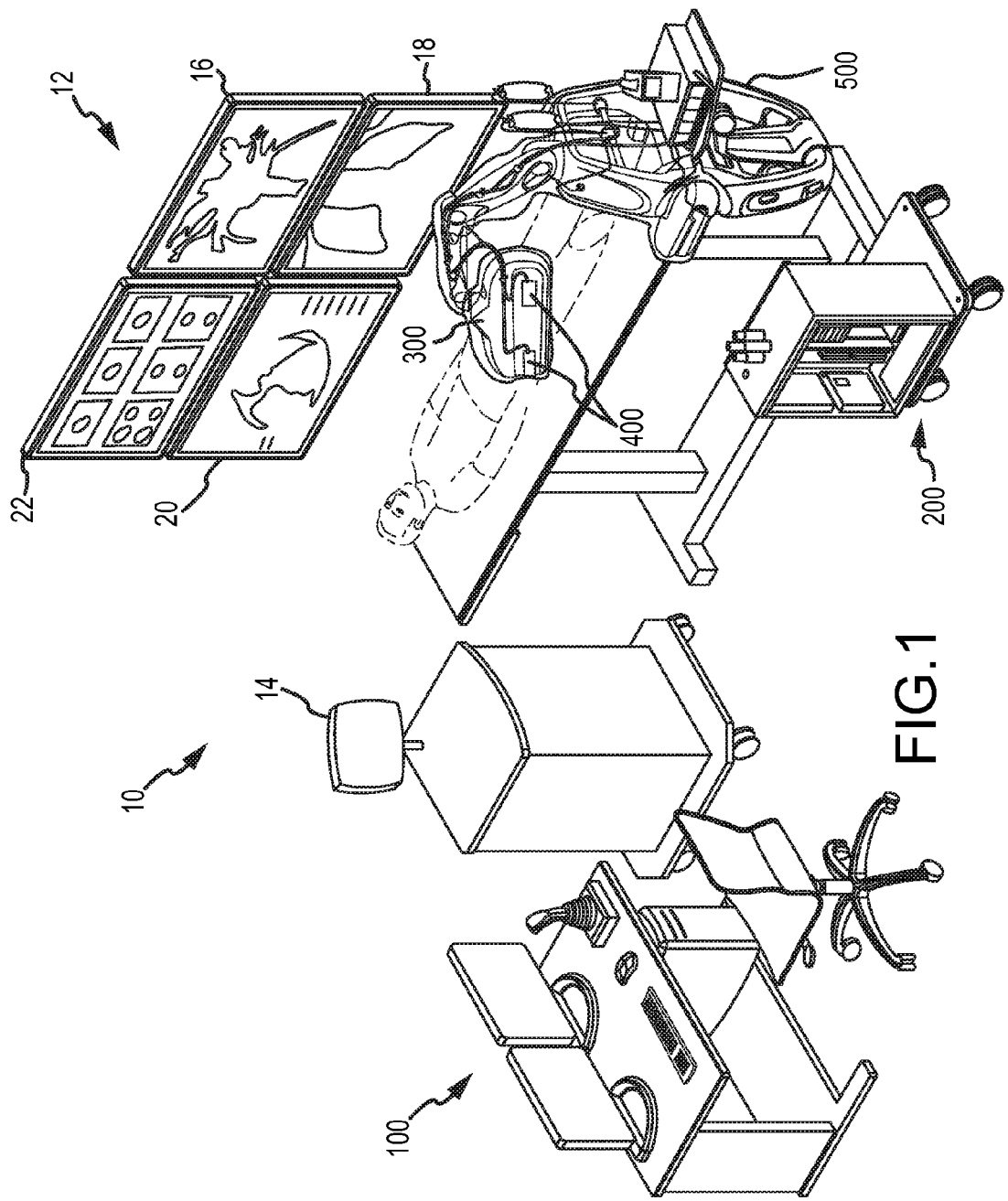
FIG. 1 is an isometric, diagrammatic view of a robotic catheter system, illustrating an exemplary layout of various system components.

Now referring to the drawings wherein like reference numerals are used to identify identical components in the various views, FIG. 1 is a diagrammatic view of an exemplary RCGS 10, in which several aspects of a system and method collision detection and avoidance can be used.

Exemplary RCGS System Description.

RCGS 10 can be likened to power steering for a catheter system. The RCGS 10 can be used, for example, to manipulate the location and orientation of catheters and sheaths in a heart chamber or in another body cavity or lumen. The RCGS 10 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target location, either the user or the system can perform the desired diagnostic or therapeutic function. The RCGS 10 enables full robotic navigation/guidance and control.

As shown in FIG. 1, the RCGS 10 can generally include one or more monitors or displays 12, a visualization, mapping and navigation (including localization) system 14, a human input device and control system (referred to as "input control system") 100, an electronic control system 200, a manipulator assembly 300 for operating a device cartridge 400, and a manipulator support structure 500 for positioning the manipulator assembly 300 in proximity to a patient or a patient's bed.

Displays 12 are configured to visually present to a user information regarding patient anatomy, medical device location or the like, originating from a variety of different sources. Displays 12 can include (1) an ENSITE VELOCITY monitor 16 (coupled to system 14—described more fully below) for displaying cardiac chamber geometries or models, displaying activation timing and voltage data to identify arrhythmias, and for facilitating guidance of catheter movement; (2) a fluoroscopy monitor 18 for displaying a real-time x-ray image or for assisting a physician with catheter movement; (3) an intra-cardiac echo (ICE) display 20 to provide further imaging; and (4) an EP recording system display 22.

The system 14 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an ENSITE VELOCITY system running a version of ENSITE NAVX® software commercially available from St. Jude Medical, Inc., of St. Paul, Minn. and as also seen generally by reference to U.S. Pat. No. 7,263,397 issued 28 Aug. 2007 to Hauck et al., hereby incorporated by reference in its entirety as though fully set forth herein. System 14 can comprise conventional apparatus known generally in the art, for example, the ENSITE VELOCITY system described above or other known technologies for locating/navigating a catheter in space (and for visualization), including for example, the CARTO visualization and location system of Biosense Webster, Inc., the AURORA® system of Northern Digital Inc., a magnetic field based localization system such as the gMPS system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties as though fully set forth herein) or a hybrid magnetic field-impedance based system, such as the CARTO 3 visualization and location system of Biosense Webster, Inc. Some of the localization, navigation and/or visualization systems can involve providing a sensor for producing signals indicative of catheter location and/or orientation information, and can include, for example one or more electrodes in the case of an impedance-based localization system such as the ENSITE VELOCITY system running NavX software, which electrodes can already exist in some instances, or alternatively, one or more coils (i.e., wire windings) configured to detect one or more characteristics of a low-strength magnetic field, for example, in the case of a magnetic-field based localization system such as the GMPS® system using technology from MediGuide Ltd. described above.

The input control system 100 is configured to allow a user, such as an electrophysiologist, to interact with the RCGS 10, in order to control the movement and advancement/withdrawal of both a catheter and sheath (see, e.g., U.S. utility patent application Ser. No. 12/751,843 filed 31 Mar. 2010 and published 7 Oct. 2010 under publication no. US 2010/0256558 A1, now pending, and PCT/US2009/038597, published 1 Oct. 2009 under publication no. WO 2009/120982; the entire disclosure of both applications being hereby incorporated by reference in their entirety as though fully set forth herein). Generally, several types of input devices and related controls can be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, U.S. utility patent application Ser. No. 12/933,063 filed 16 Sep. 2010 and published 20 Jan. 2011 under publication no. US 2011/0015569 A1, now pending, and U.S. utility patent application Ser. No. 12/347,442 filed 31 Dec. 2008 and published 1 Oct. 2009 under publication no. US 2009/0248042 A1, now pending, the entire disclosure of both applications being hereby incorporated by reference in their entirety as though fully set forth herein. The input devices can be configured to directly control the movement of the catheter and sheath, or can be configured, for example, to manipulate a target or cursor on an associated display.

The electronic control system 200 is configured to translate (i.e., interpret) inputs (e.g., motions) of the user at an input device or from another source into a resulting movement of the catheter and/or surrounding sheath. In this regard, the system 200 includes a programmed electronic control unit (ECU) in communication with a memory or other computer readable media (memory) suitable for information storage. Relevant to the present disclosure, the electronic control system 200 is configured, among other things, to issue commands (i.e., actuation control signals) to the manipulator assembly 300 (i.e., to the actuation units electric motors) to move or bend the catheter and/or sheath to prescribed positions and/or in prescribed ways, all in accordance with the received user input and a predetermined operating strategy programmed into the system 200. In addition to the instant description, further details of a programmed electronic control system can be found in U.S. utility patent application Ser. No. 12/751,843 filed 31 Mar. 2010 and published 7 Oct. 2010 under publication no. US 2010/0256558 A1, now pending, described above. It should be understood that although the exemplary ENSITE VELOCITY System 14 and the electronic control system 200 are shown separately, integration of one or more computing functions can result in a system including an ECU on which can be run both (i) various control and diagnostic logic pertaining to the RCGS 10 and (ii) the visualization, mapping and navigation functionality of system 14.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly can be found in U.S. utility patent application Ser. No. 12/347,826 filed 31 Dec. 2008 and published 1 Oct. 2009 under publication no. US 2009/0247942 A1, now pending, which is hereby incorporated by reference in its entirety as though fully set forth herein. Although the manipulator 300 is illustrated and described with respect to the manipulation of a single medical device (e.g., a single catheter and sheath combination), the manipulator 300 can be configured to manipulate multiple devices, such as a cardiac mapping catheter, an ablation catheter, an imaging catheter, such an intracardiac echocardiography (ICE) catheter, or the like.

A device cartridge 400 is provided for each medical device controlled by the RCGS 10. For this exemplary description of an RCGS, one cartridge is associated with a catheter and a second cartridge is associated with an outer sheath. The cartridge is then coupled, generally speaking, to the RCGS 10 for subsequent robotically-controlled movement. In addition to the description set forth herein, further details of a device cartridge can be found in U.S. utility patent application Ser. No. 12/347,835 filed 31 Dec. 2008 and published 1 Oct. 2009 under publication no. US 2009/0247943 A1, now pending, and U.S. utility patent application Ser. No. 12/347,842 filed 31 Dec. 2008 and published 1 Oct. 2009 under publication no. US 2009/0247944 A1, the entire disclosure of both applications being hereby incorporated by reference in their entirety as though fully set forth herein.

Figure 2:
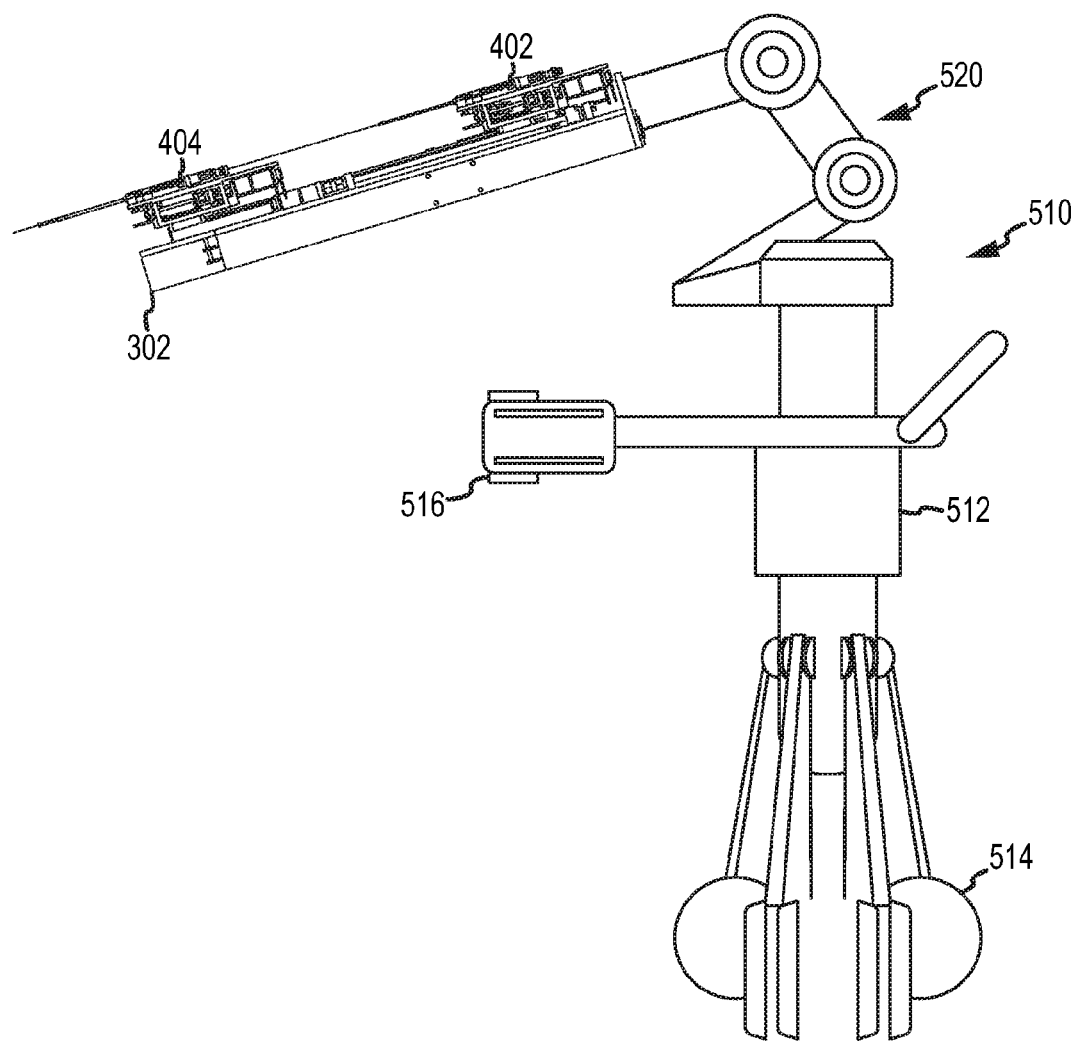
FIG. 2 is a side view of a manipulator assembly shown in FIG. 1, coupled to a robotic support structure, showing side views of catheter and sheath manipulation mechanisms.

FIG. 2 is a side view of an exemplary robotic catheter manipulator support structure, designated structure 510 (see U.S. utility patent application Ser. No. 12/347,811 filed 31 Dec. 2008 and published 1 Oct. 2009 under publication no. US 2009/0247993 A1, described above). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 3A:
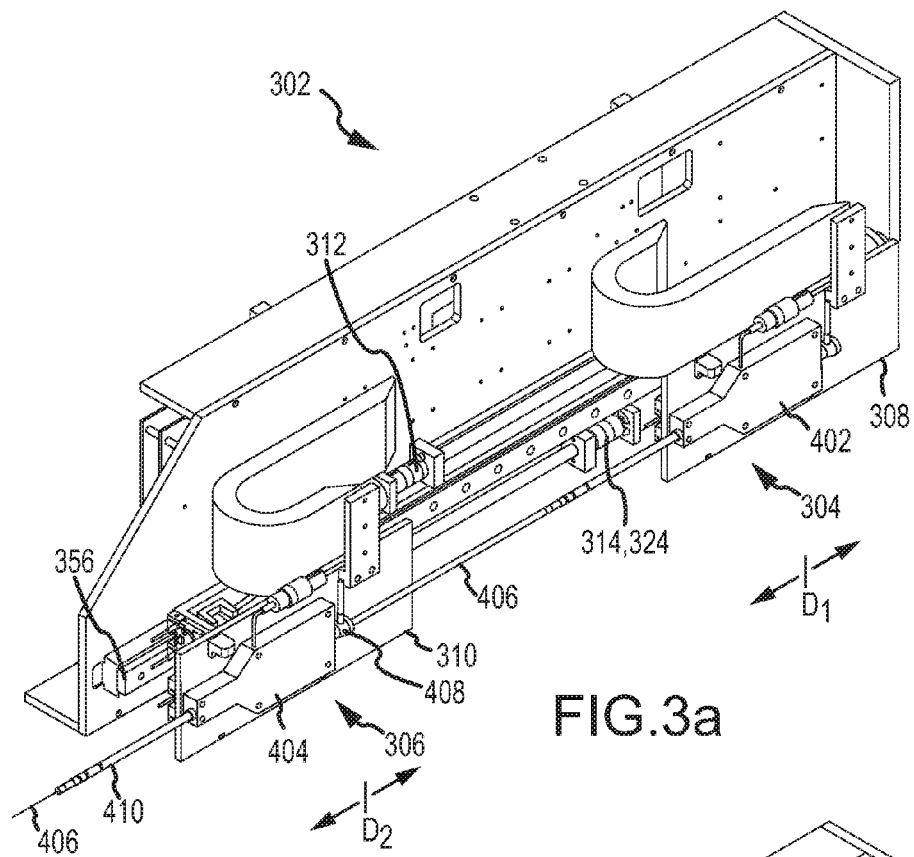
FIGS. 3a-3b are isometric views of a manipulator assembly shown in FIG. 2, showing the catheter and sheath manipulation mechanism in greater detail.
Figure 3B:
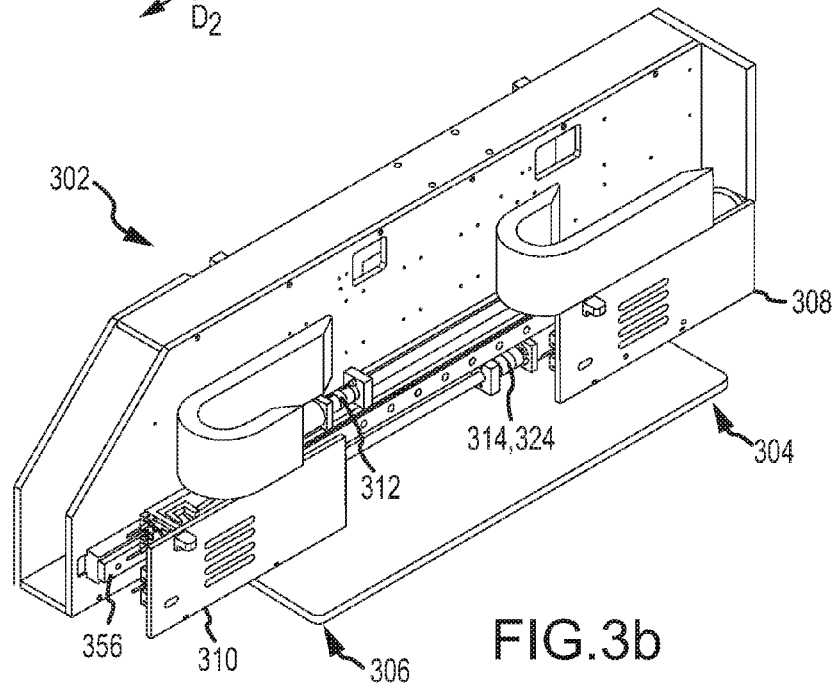
Figure 4A:
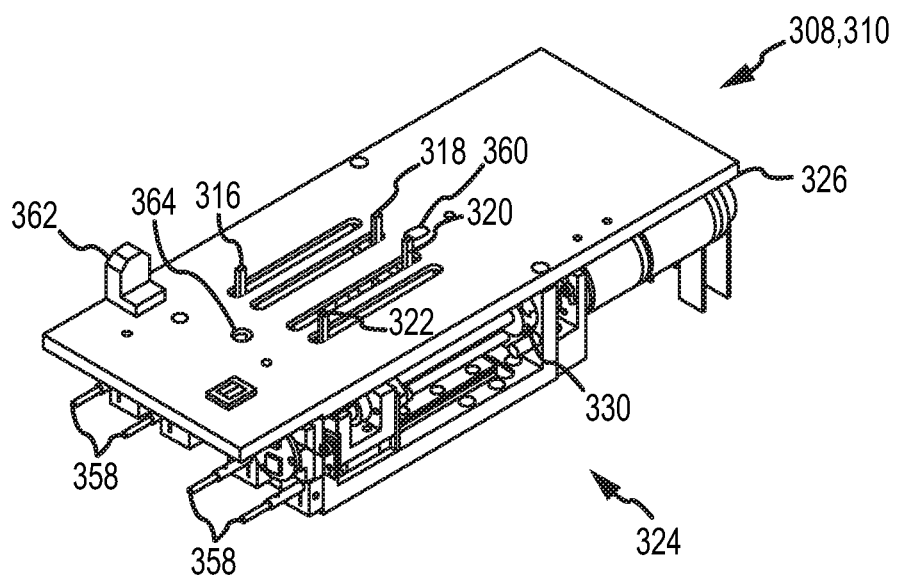
FIGS. 4a-4c are isometric views showing a sheath manipulation base of FIGS. 3a-3b in greater detail.
Figure 4B:
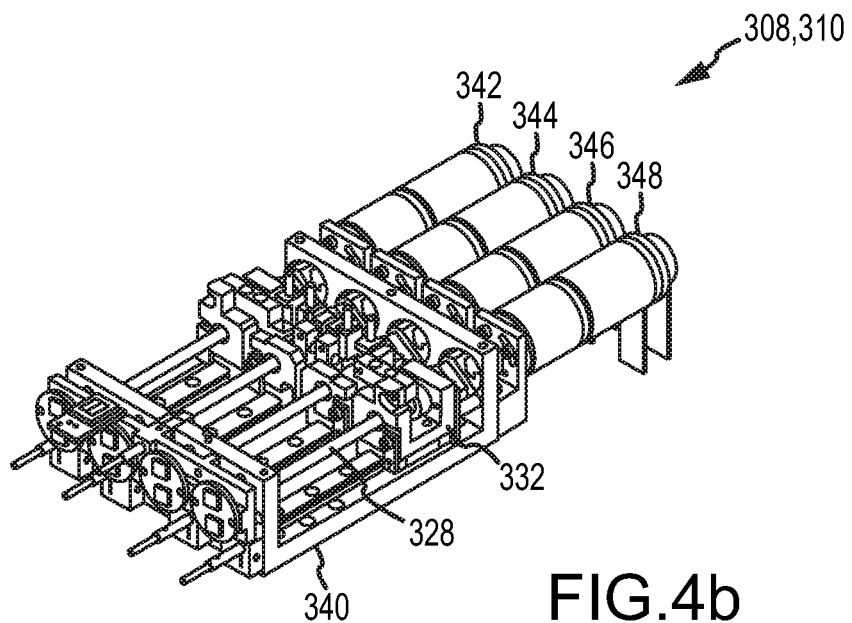
Figure 4C:
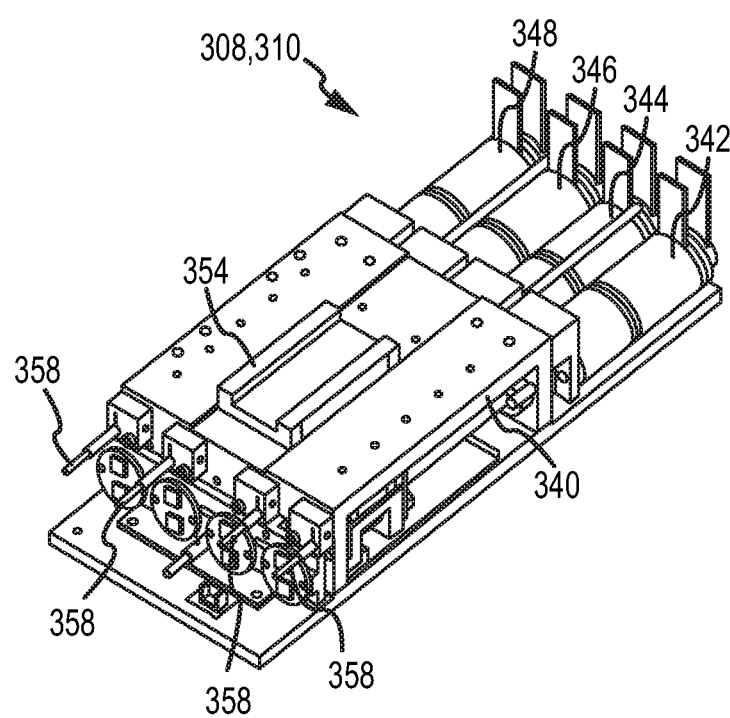
Figure 5A:
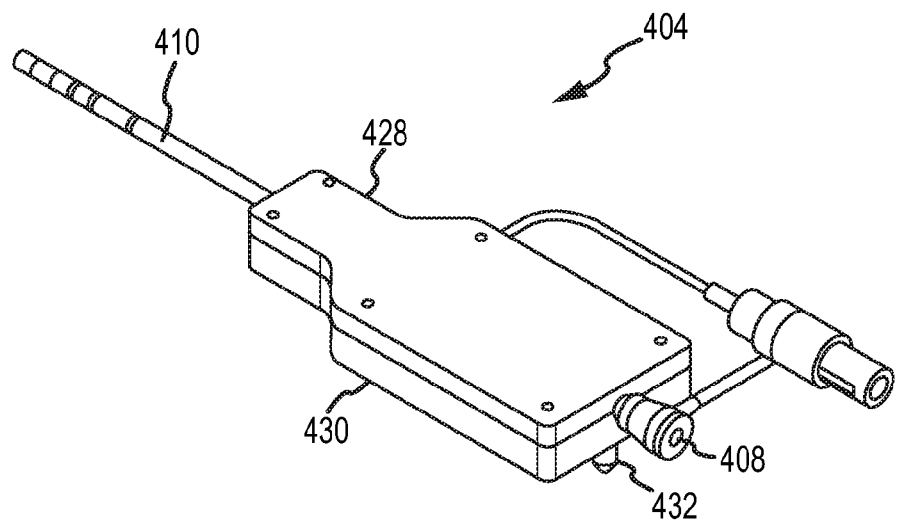
FIGS. 5a-5b are isometric views showing a sheath, cartridge of FIGS. 3a-3b in greater detail.
Figure 5B:
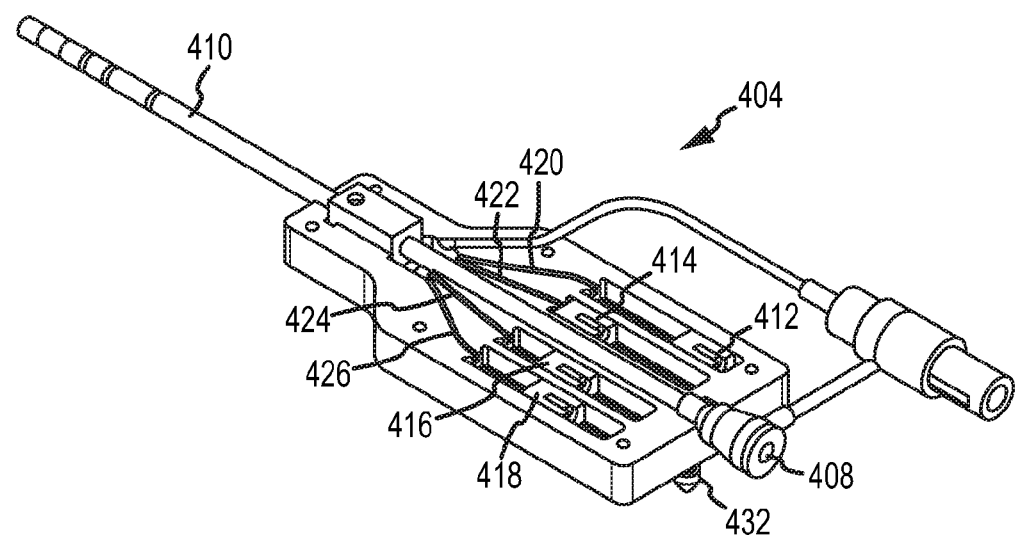

In the Figures to follow, FIGS. 3a-3b will show a manipulator assembly, FIGS. 4a-4c will show a manipulation base, and FIGS. 5a-5b will show a device cartridge.

FIG. 3a is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 3a. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation, for example, can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in PCT/US2009/038597, published 1 Oct. 2009, as WO 2009/120982, which is hereby incorporated by reference in its entirety as though fully set forth herein.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 3b is an isometric view of manipulator assembly 302, substantially the same as FIG. 3a except that catheter and sheath cartridges 402, 404 are omitted (as well as catheter and sheath 406, 410) so as to reveal an exposed face of the manipulation bases 308, 310.

FIG. 4a is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks, such as slider blocks 412, 414, 416, 418 best shown in FIG. 5b, to independently tension select steering wires 420, 422, 424, 426, also best shown in FIG. 5b. Each finger can be configured to be independently actuated (i.e., moved back and forth within the oval slots depicted in FIG. 4a) by a respective precision drive mechanism, such as a motor driven ball screw 324. A plate 326 provides a surface onto which one of the cartridges 402, 404 are seated.

FIG. 4b is an isometric, enlarged view of base 308 (and base 310), substantially the same as FIG. 4a except with plate 326 omitted. Each motor-driven ball screw 324, best shown in FIG. 4a, for both finger control and for cartridge translation control, can further include encoders to measure a relative and/or an absolute position of each element of the system. Moreover, each motor-driven ball screw 324, for both finger control and cartridge translation control, can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. These and other types of remote actuation can directly benefit from the teaching of the instant disclosure.

FIG. 4c is an isometric, enlarged view of base 308 (and base 310) that is taken from an opposite side as compared to FIGS. 4a-4b. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 5a is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 5b is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (e.g., four) steering wires. Device cartridges 402, 404 can be provided as a disposable item that is capable of being easily positioned (e.g., snapped) into place onto a respective base 408, 410. Sheath cartridge 404 can be designed in a similar manner as the catheter cartridge 402, but will typically be configured to provide for the passage of catheter 406.

Referring to FIGS. 4a and 5a, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 5a) on the cartridge can engage one or more mating recesses 360 in the base (see FIG. 4a). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 4a).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 5b). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 10.

Figure 6:
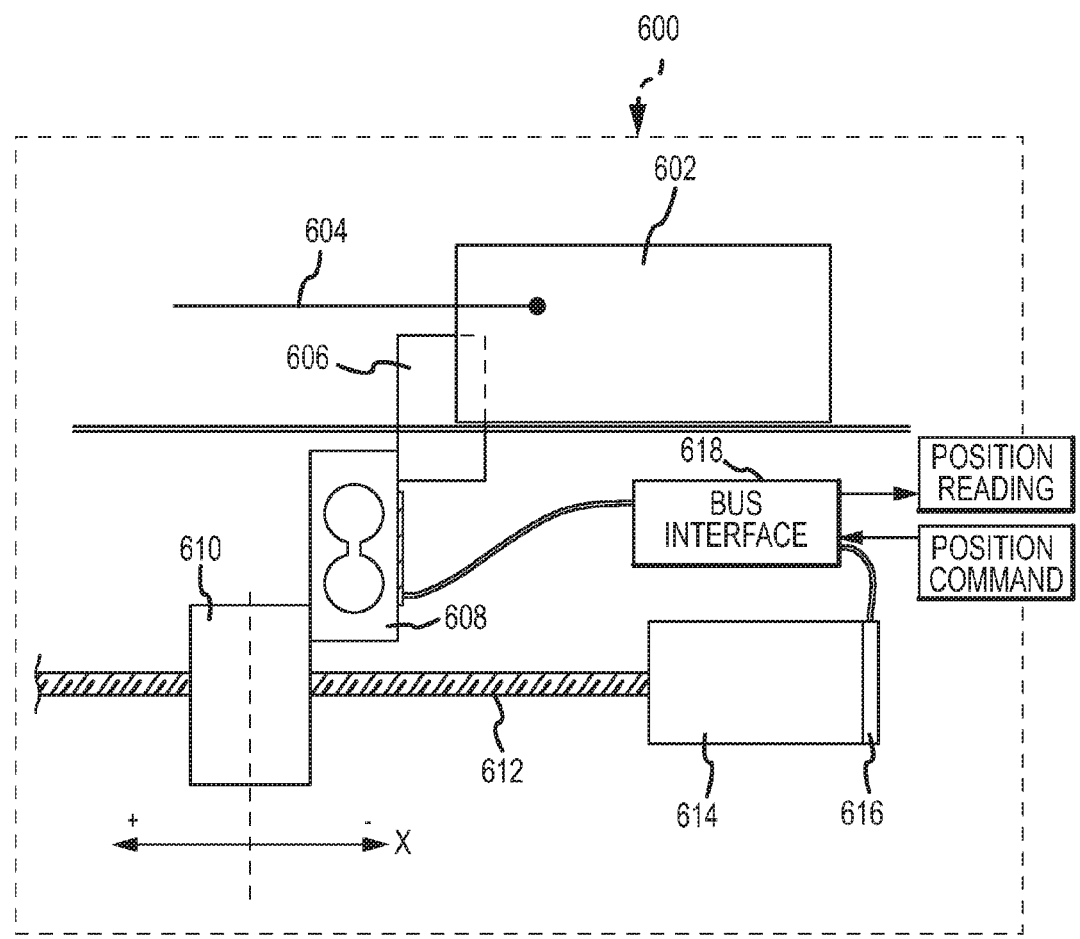
FIG. 6 is a diagrammatic view of the sheath manipulation mechanism of FIG. 2.

FIG. 6 is a diagrammatic view of a node suitable for connection to a communications bus (not shown) in RCGS 10. The node includes an actuation unit 600, similar to the actuation mechanisms described above (e.g., catheter actuation mechanism 304). In an embodiment, the RCGS 10 can have at least ten such actuation units (i.e., one for each of the four catheter steering wires, four sheath steering wires, one catheter manipulation base and one sheath manipulation base), which as described include electric motors. Of course, as described above, when the RCGS 10 is configured to manipulate multiple medical devices, each medical device will include a respective actuation assembly, suited to the type of medical device.

FIG. 6 shows in diagrammatic or block form many of the components described above—where appropriate, references to the earlier describe components will be made. Actuation unit 600 includes a first, slidable control member 602 (e.g., the slider as described above) that is connected to or coupled with a second, tensile control member 604 (e.g., the steering wire as described above). The slider 602 can be configured to interface with a third, movable control member 606 (e.g., the finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 also includes a rotary motor position encoder 616 that is coupled to the motor 614 and is configured to output a signal indicative of the position of the motor 614. The encoder 616 can comprise an internal, optical encoder assembly, integral with motor 614, configured to produce a relatively high accuracy output. The motor position sensor can operate in either absolute or relative coordinates. In an embodiment, a second motor position sensor (not shown) can also be provided, such as a potentiometer (or impedance-based), configured to provide a varying voltage output proportional to the motor's rotary position. The output of the secondary position sensor can be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 200 (via the bus). The controller communicates with the main electronic control system 200 via the bus interface and is configured, among other things, to (1) receive and execute motor actuation commands issued by the electronic control system 200 for controlling the movements of motor 614; and (2) receive and execute a command (issued by the electronic control system 200) to take a motor position sensor reading, for example, from encoder 616 and subsequently report the reading to system 200.

Collision Detection and Avoidance System in the RCGS.

An apparatus for use in the RCGS 10 as described herein minimizes or eliminates unintended collision between a medical device (e.g., catheter) and an object, which may also be a medical device but can also be an anatomical feature in the body of the patient. Avoiding collision reduces or eliminates device entanglement and/or unintended tissue trauma.

Figure 7:
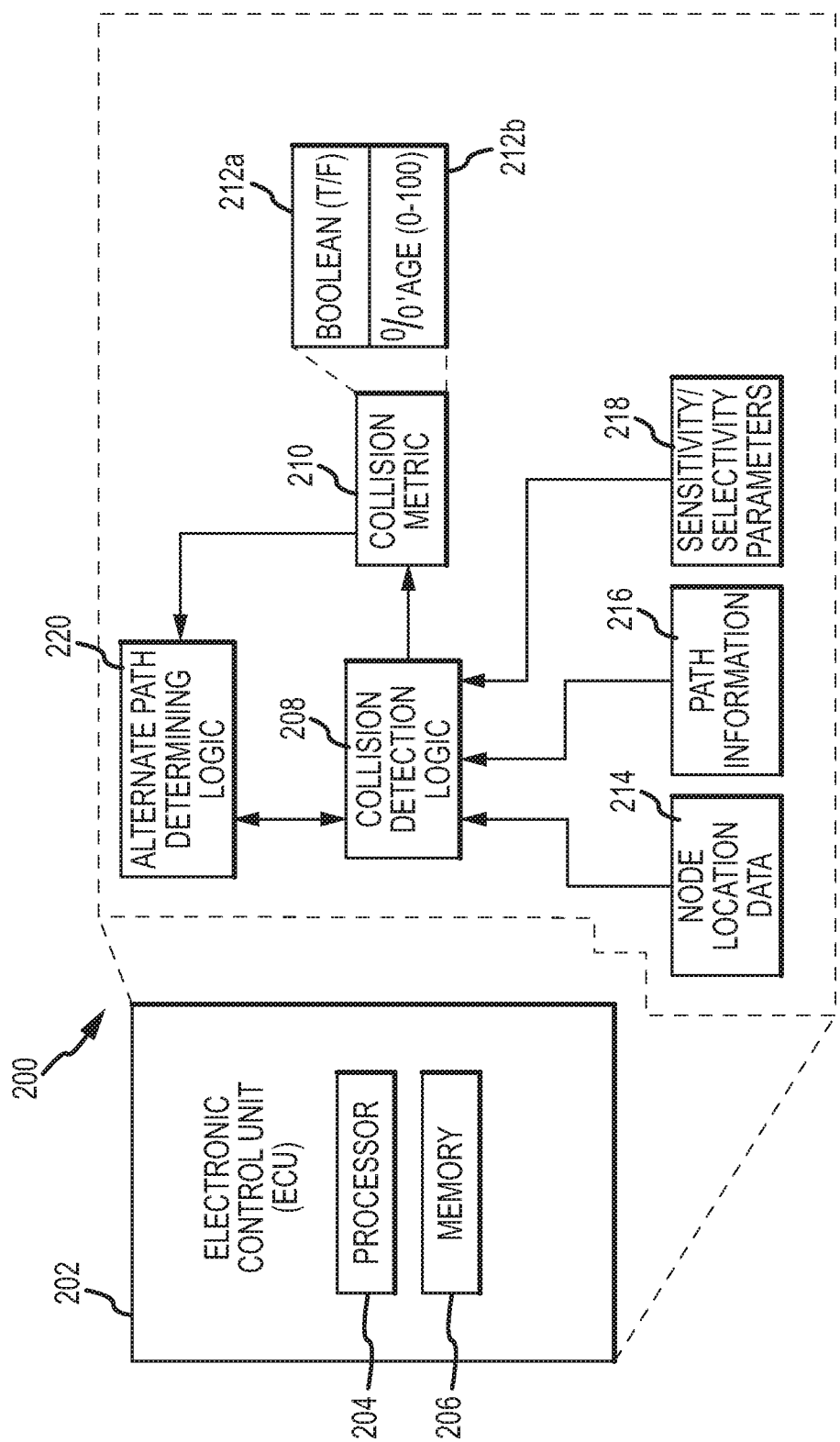
FIG. 7 is an exemplary block diagram view of a system for detecting a collision between a medical device and an object.

FIG. 7 is a block diagram showing electronic control system 200 of FIG. 1, in which embodiments of the collision detection and avoidance system can be implemented. The system 200 includes an electronic control unit (ECU) 202 having a processor 204 and an associated computer-readable memory structure 206. The system 200 further includes collision detection logic 208, which in an embodiment can take the form of software stored in memory 206 and configured for execution by the processor 204. The ECU 202 can comprise conventional apparatus known in the art. In an embodiment, the ECU 202 is configured to perform not only the collision detection and avoidance functions described herein, but also the core operating functions of the RCGS 10. It should be appreciated, however, that these functions can be implemented in a distributed computing environment where separate processing units perform different functions.

As to the core RCGS functions, the ECU 202 is configured to interpret user inputs, device location data, motor position readings as well as other inputs and generate a plurality of actuation control signals (see, e.g., FIG. 6: "position commands"), which are provided to the manipulator assembly 300. The actuation control signals, in turn, are configured to control a plurality of electric motors (e.g., motor 614 in FIG. 6 being one) so as to actuate a plurality of control members of the medical device being manipulated (e.g., pull wires for deflection movement, manipulation bases for translation movement). While the exemplary RCGS 10 includes robotic control mechanisms for guiding the movement of both a catheter and a sheath, embodiments can be used in connection with a wide range of medical devices in addition to a catheter and a sheath. However, for ease of description, the medical device will be referred to as a catheter. Additionally, the RCGS 10 can be configured to control and otherwise manipulate a plurality of medical devices.

With continued reference to FIG. 7, collision detection logic 208 is configured to determine a collision metric 210 indicative of a collision between a medical device and an object. In an embodiment, the medical device may comprise a catheter, although the present invention is not so limited. The object may also be a medical device (either manipulated by RCGS or manually by a physician), or an anatomical structure within the body of the patent (e.g., heart chamber wall). The collision detection logic 208 is configured to use virtual representations of both the medical device and the object in determining collision (and thus the collision metric), all in accordance with a predetermined detection strategy. The collision metric 210 may take the form of a Boolean (i.e., true meaning a collision, or false—meaning no collision) or a fuzzy collision metric having a value, for example, between 0-100%. The fuzzy collision metric will be described in greater detail below.

In generating the collision metric, the collision detection logic 208 is further configured to process a variety of input information, such as node location data from block 214, pre-planned path information from block 216 and sensitivity and/or selectivity parameter values from block 218. In an embodiment, alternate path determining logic 220 is configured to generate an alternate path for a medical device when the pre-planned path is predicted by logic 208 to collide during movement along the pre-planned path. Alternate path determining logic 220 is configured to generate such an alternate path and/or path (alternate or otherwise) in combination with an action (e.g., catheter retraction into a sheath) so as to avoid a collision.

Node location data from block 214 can comprise location data, such as position and orientation information, associated with one or more position sensors disposed along or within a manipulated medical device, such as a catheter. In an embodiment where an impedance-based localization system 14 (e.g., ENSITE VELOCITY) is used as the source, the location data can comprise at least an electrode coordinate (x, y, z) for specified electrodes on the catheter. It should be understood, however, that the RCGS system 10 can utilize other navigation and/or localization technologies, such as CARTO or GMPS®, which are magnetic-field based localization systems, or still others, such as magnetic resonance imaging (MRI) and ultrasound-based tracking. Accordingly, in view of the wide range of localization technologies that may be used, the position sensor may be selected from the group comprising an electrically-conductive electrode, an electromagnetic field sensor, a magnetic resonance imaging tracking coil, a marker detectable in fluoroscopic imaging, and an ultrasound transducer. Moreover, each position sensor will herein be referred to as a node. In this regard, nodes can also be generated from known catheter data. For instance, a catheter may have ten (10) electrodes arranged in five (5) electrode pairs, with the pairs being spaced apart by a known distance, such as for example 1 mm. The system herein may be configured to recognize the 1 mm space between an electrode pair as a node. Such location information can be used in determining a virtual representation of the medical device (or devices) for collision detection purposes.

In an embodiment, the system 14 from which node location data 214 obtains such data, may comprise an electro-anatomical modeling system, such as an electric field-based system, such as, for example, the ENSITE NAVX® system commercially available from St. Jude Medical, Inc., and generally shown with reference to U.S. Pat. No. 7,263,397 issued 28 Aug. 2007, the entire disclosure of which is hereby incorporated by reference in its entirety as though fully set forth herein. In other exemplary embodiments, however, the system 14 may comprise other types of systems, such as, for example and without limitation: a magnetic-field based system such as the CARTO System available from Biosense Webster, and as generally shown with reference to one or more of U.S. Pat. Nos. 6,498,944, 6,788,967 and 6,690,963, the entire disclosures of which are hereby incorporated by reference in their entirety as though fully set forth herein, or the GMPS® system from MediGuide Ltd., and as generally shown with reference to one or more of U.S. Pat. Nos. 6,233,476, 7,197,354, and 7,386,339, the entire disclosures of which are hereby incorporated by reference in their entirety as though fully set forth herein; a combination electric field-based and magnetic field-based system such as the CARTO 3 System also available from Biosense Webster; as well as other impedance-based localization systems, acoustic or ultrasound-based systems, and commonly available fluoroscopic, computed tomography (CT), and magnetic resonance imaging (MRI)-based systems. A localization system 14 for use herein can be a system as generally shown with reference to U.S. utility patent application Ser. No. 13/338,374 filed 28 Dec. 2011, the entire disclosure of which is hereby incorporated by reference in its entirety as though fully set forth herein.

Path information block 216 is configured to determine and provide information relating to a pre-planned path for one or more medical devices. For example, an user interface (UI—not shown) displays information regarding a currently displayed (rendered) scene (e.g., the view angle, the mouse location, the catheter tip location, etc.). The UI is further configured to receive user inputs with respect to an anatomical model of a body portion of the patient, for example, for setting up a pre-planned path for the catheter, for initiating and conducting diagnostic and therapeutic procedures, or the like. The pre-planned path may include information describing a current, a target location, and a trajectory or path describing the taken by the distal tip of the medical device as RCGS 10 manipulates the medical device. As the distal tip traverses the pre-planned path, the medical device takes on a plurality of poses.

Sensitivity/selectivity parameter block 218 is configured to provide information used to configure the operation of the collision detection logic 208 in generating the collision metric 210 so as to become more sensitive to possible collision (i.e., with perhaps some false positives as the sensitivity increases) and/or more selective in detecting collision (i.e., perhaps with some false negatives). Examples of such parameters will be set forth below.

Collision Detection.

Figure 8A:
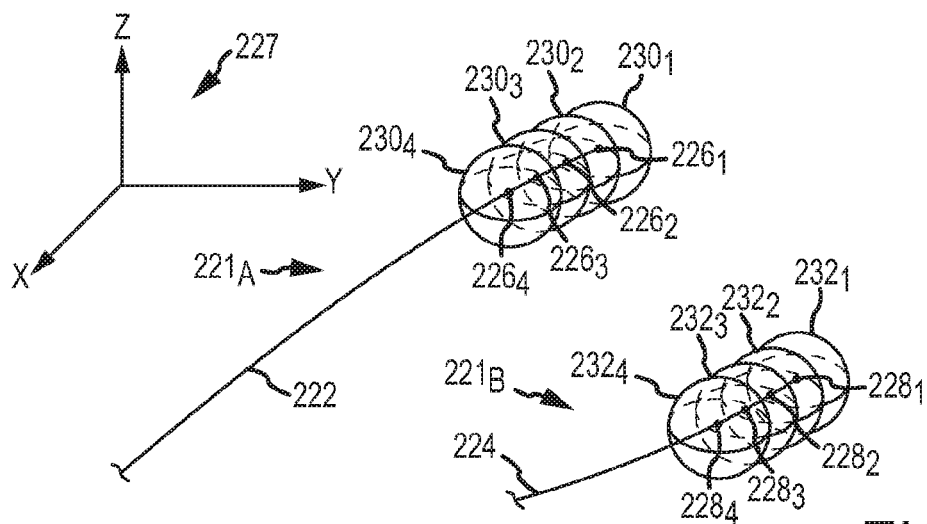
FIG. 8A is a schematic diagram illustrating a collision, detection method employing geometrical solids to simulate device surfaces.
Figure 8B:
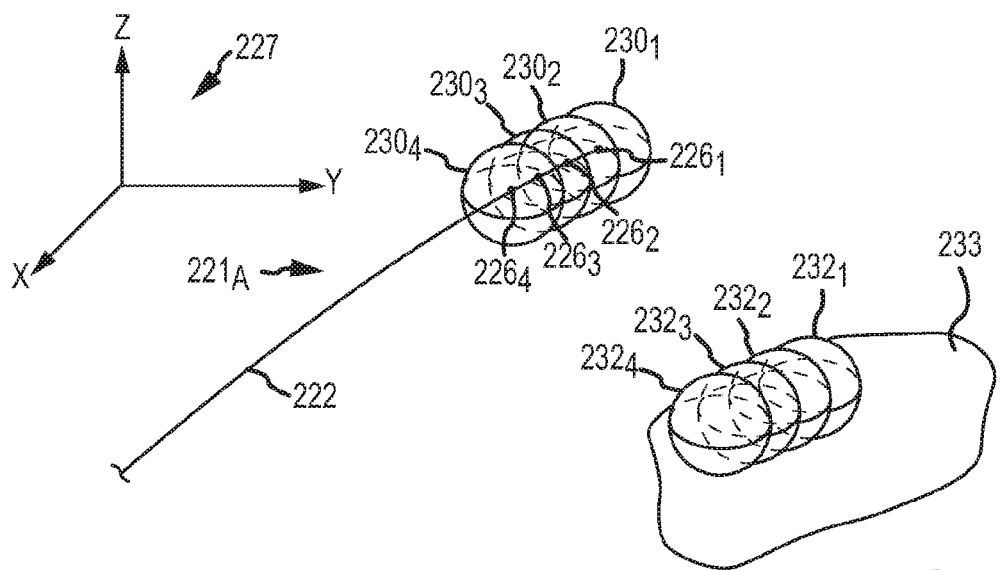
FIG. 8B is a schematic diagram illustrating a collision detection method employing geometrical solids to simulate a device surface and a cardiac geometry surface representing a tissue surface.

FIGS. 8A-8B are schematic diagrams illustrating a collision detection technique that uses virtual representations of the objects being tested for collision. FIG. 8A represents collision detection with respect to two medical devices. FIG. 8B represents collision detection with respect to a medical device and a cardiac geometry.

In an embodiment, one approach for detecting collisions is to represent the surface of the objects under consideration (e.g., medical devices) with simple geometrical shapes, such as spheres or the like, arranged so as to approximate the surface of the object under consideration. For example, FIG. 8A shows a first virtual representation of a first catheter $221_A$, for example, including a spline 222 and a second virtual representation of a second catheter $221_B$, for example, including a spline 224. In the case of catheters represented in a cardiac navigation system, a catheter is usually defined as a spline that passes through several position sensor elements (i.e., the nodes as described above). For example, the first catheter $221_A$ in FIG. 8A includes a plurality of nodes designated $226_1$, $226_2$, $226_3$, $226_4$, ..., $226_n$, and the second catheter includes a plurality of nodes designated $228_1$, $228_2$, $228_3$, $228_4$, ..., $228_n$. In an impedance-based navigation and localization system embodiment (e.g., ENSITE NAVX®), the positioning sensors comprise electrodes, which allow measurement and determination of a position coordinate for each electrode. In FIGS. 8A-8B, a reference coordinate system 27 comprises a Cartesian coordinate system. While there different approaches known in the art for achieving a spline fit, in the impedance-based navigation and localization embodiment, a spline fit function already exists for at least the purpose of visually rendering the device for purposes of display. In addition, while the spheres may be touching with no overlap, in an embodiment, the spheres may be overlapping by a predetermined amount (e.g., 50% with respect to the diameter of the spheres).

In particular, a catheter may be visually rendered on a display by fitting the set of electrode or node locations with a B-spline. The B-spline is a curve that passes through each node (electrode) location with minimal oscillations. Being a two dimensional (2D) curve, a series of connected cylinders centered on the spline can then be and typically is used to visually render a catheter with mass. This is a typical configuration for impedance-based navigation and localization system 14.

With continued reference to FIG. 8A, in addition to the splines, the virtual representations of the devices further include a plurality of geometrical solids representing the surface of the object (e.g., catheter). While a system 14 may employ cylinders as mentioned above, in an embodiment, the virtual representation of the device, the geometrical solids used for collision detection comprises spheres, for example, a plurality of spheres designated $230_1$, $230_2$, $230_3$, $230_4$, ..., $230_n$. Likewise, the outer surface of the second catheter can also be represented by the same type and size of geometrical solid, such as spheres, for examples, such as spheres, $232_1$, $232_2$, $232_3$, $232_4$, ..., $232_n$.

With this information for context, collision detection between devices can be reduced to testing for collision between all combinations of the geometrical solids (e.g., cylinders, spheres) associated with the respective devices. In an embodiment where the geometrical solids comprise spheres, the test for collision between two spheres reduces to a distance test. In particular, the collision detection logic 208 can be configured to evaluate equation (1) below, which if true, indicates collision:

$$\sqrt{(x-y)^2} < (r+s) \quad (1)$$

where a first sphere from the first plurality of spheres $230_1$, $230_2$, $230_3$, $230_4$, ..., $230_n$ is defined on the first spline 222 and has a center location x (in the reference coordinate system 227) and a radius r, and where a second sphere of the second plurality of spheres $232_1$, $232_2$, $232_3$, $232_4$, ..., $232_n$ is defined on the second spline 224 and has a center location y in the reference coordinate system 227 and a radius s.

Alternatively, the formula in equation (1) can be rewritten as equation (2) below, which is less computationally intensive as it avoids the calculation of a square root:

$$(x-y)^2 < (r+s)^2, \quad (2)$$

Thus, for collision detection, in an embodiment, each object (e.g., catheters $221_A$ or $221_B$) can be represented as a series of spheres or cylinders that are centered on the same spline. The use of spheres may not provide an optimal visual representation of a catheter (like the cylinder), inasmuch as the diameter of the resulting, visually-rendered catheter would tend to oscillate as one sphere falls off and the next sphere takes over. However, the spheres that represent the catheter for detection purposes need not be visually displayed at all, and can remain hidden and only used for the calculation and detection of collisions.

Alternatively, the plurality of cylinders that are typically used to visually represent or depict a catheter (i.e., more generally, an object) could also be used for collision detection, for example, by also determining whether cylinders associated with respective objects intersect, thus indicating collision. The calculation of the intersection of two cylinders is considerably more complicated, however, than that required for two spheres. The choice of using spheres versus cylinders, or any other geometrical solid for that matter, corresponds to a tradeoff between computational intensity and accuracy. In general, the accuracy obtained by using spheres can be improved by increasing the number of spheres used at the expense of more distance comparisons. In this regard, sensitivity/selectivity block 218 may be include parameter values specifying the number of spheres to use during the execution of the detection strategy by the collision detection logic 208.

The devices or objects that are tested for collision can be represented, more generally, through the use of a wide variety of geometrical solids. For example, instead of spheres, the medical device or object can be represented as a collection of any geometrical solid, such as a cube, a tetrahedron, a cone and the like. The particular type of geometrical solid used will depend on the particular application, but in general the most straightforward approach is to use spheres.

FIG. 8B depicts the collision detection described but now as between a catheter, on the one hand, and a cardiac geometry 233, which represents the tissue surface of the heart (or chambers or features of the heart). The processing described above in connection with FIG. 8A applies with equal force to the situation depicted in FIG. 8B.

Figure 9:
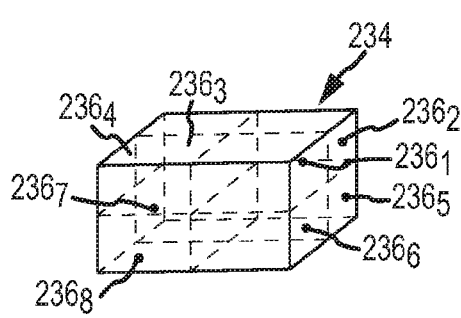
FIG. 9 is a diagrammatic view showing a volume subdivided into cells where such cells can be used in an oct-tree search for reducing the number of collision tests needed.

FIG. 9 is a diagrammatic view of a volume in which a plurality of medical devices may reside, partitioned into smaller cells for the purpose of reducing the number of collision checks. As mentioned above, in certain collision detection embodiments, for example, using non-spherical geometrical solids, involve a significant amount of calculation power (i.e., processing power). A reduced processing burden, and thus an increased decision-making speed for the collision detection algorithm, can be made using an Oct-tree technique. The volume in which the devices lie, for example, the volume designated 234, is recursively partitioned into eight cubes or cells inside the higher level cube. For example, the volume 234 is shown sub-divided into eight equal-size cells designated $236_1$, $236_2$, $236_3$, ..., $236_8$. The Oct-tree technique operates to reduce the overall number of comparisons that need to be made, thereby making a corresponding reduction in the number of calculations and thus reduces the computing burden on the processor. The spheres associated with each device that are to be compared have a membership in one cell or possibly more cells if they are on a boundary of multiple cells. The filtering occurs in the first instance when only spheres from different devices that reside in the same cell(s) are compared with each other. This is because spheres from different cells are a priori known not to be in collision. It should be understood that this technique is not limited to those techniques involving non-spherical solids, as this filtering technique benefits any detection approach.

Thus, the collision detection logic 208 is configured to perform a method including the following steps. (1) determining the volume in a reference coordinate system in which at least a portion of multiple medical devices or objects reside; (2) partitioning the volume into a plurality of cells, which can be equal size cells; (3) identifying those cells in which solids (e.g., spheres) from both devices being compared reside (e.g., spheres from both the first and second pluralities of spheres); and (4) evaluating the collision detection equation (e.g., equations (1) or (2) herein in the case of a sphere) but only with respect to those identified cells from step (3). Through the foregoing, the number of calculations need to completely assess collision is reduced, thereby reduced the time it takes to perform the collision detection.

Collision Prediction.

Once the capability of detecting collision has been established, additional features can be added. For example, logic 208 can be further configured to predict collisions with respect to a pre-planned path. If the RCGS 10 is configured to move the distal tip of the medical device along a pre-planned path or trajectory between a current location (the device taking on an initial pose) and a target location (the device taking on a final pose), the device will also take on a series of intervening poses during its travel, as a result of the RCGS manipulation. With this information, logic 208 can test for collision at several intervening points during the movement along the pre-planned path, instead of just testing for collision at the current location. In other words, the logic 208 is configured to test for collision at a series of positions (poses) that the device will assume in the future, if the RCGS 10 manipulated the device along the pre-planned path to get to the target location. For clarity, while current positions of the nodes are measured, future positions of the nodes are predicted. For the purposes of predicting future positions, the path is generally planned as straight line between the current position and the target. If there is an obstruction, this planned path may be curved. This planned path is generally the path of the catheter distal tip. This path can be subdivided into arbitrarily small intermediate points. At each intermediate point the automatic control algorithm can determine the necessary pull-wire positions necessary to achieve this point via inverse kinematics. Once the position of each pull wire is determine the system can predict the complete pose of the catheter using forward kinematics. One embodiment of the inverse kinematics and the forward kinematics may be seen by reference to PCT Int'l Pub. No. WO/2011/123669 published on 10 Jun. 2011, and hereby incorporated by reference in its entirety as though fully set forth herein.

If the collision detection logic 208, through an evaluation of the series of future poses, detects a collision, then alternate path determining logic 220, responsive to detection of a collision, is operative to determine an alternative path for the device to reach the target location. Once the alternate path (or path in combination with a device action, such as catheter retraction into a sheath), has been determined, this alternative path can also be tested for collision by logic 208. The collision detection logic 208 and an alternate path determining logic 220, will continue to generate path solutions for the device to reach the target location until an alternate path is found that is able to reach the target location without encountering a collision. An embodiment of an alternate path determining logic 220 will be described below.

Figure 10:
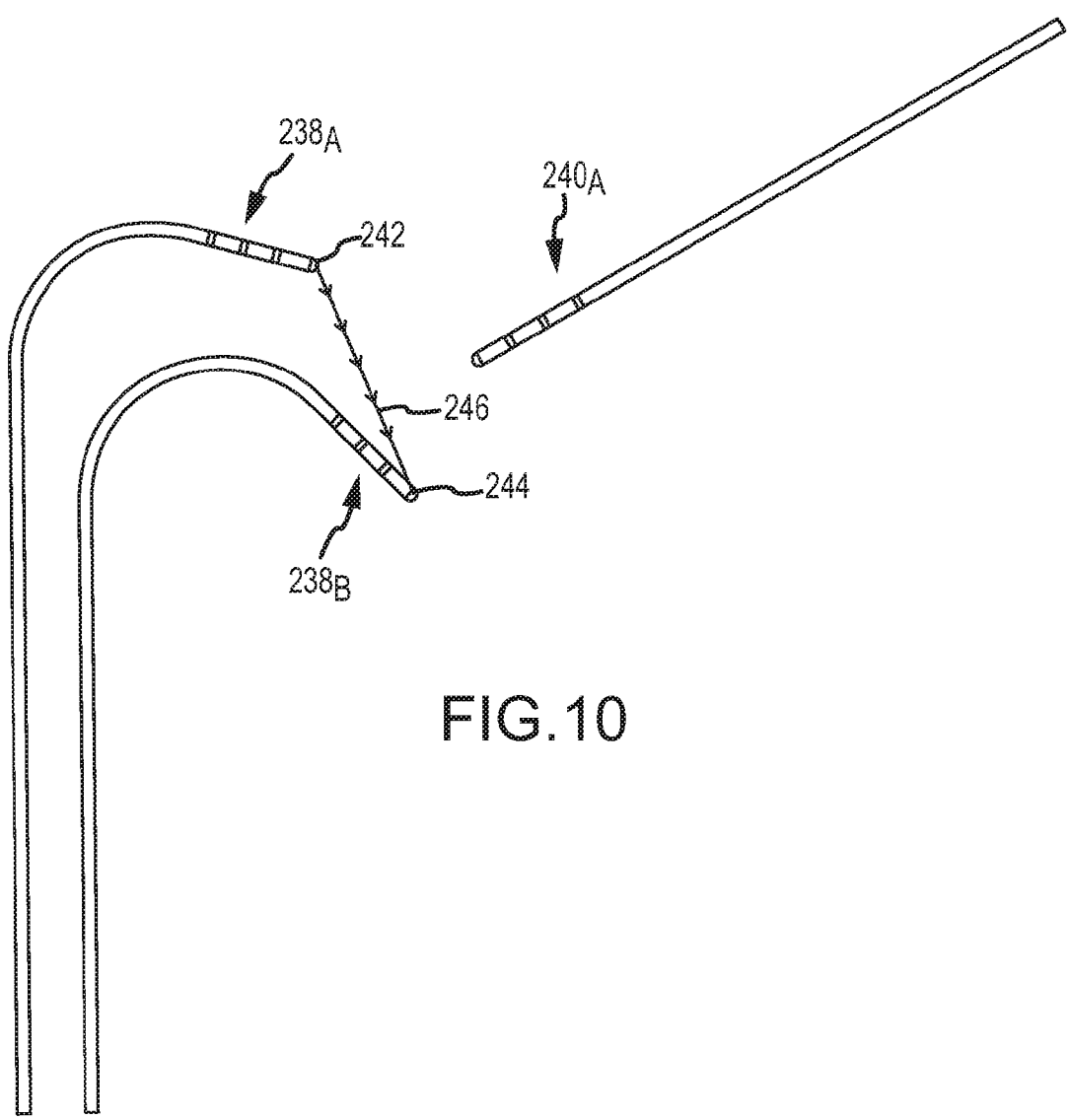
FIG. 10 is a diagrammatic view of a first catheter, in relation to a second catheter, that takes on a plurality of poses, without collision, during movement along a pre-planned path from a current location to a target location.

FIG. 10 is a diagrammatic view of a first catheter in relation to a second catheter where the first catheter assumes a plurality of different poses during movement of its distal end along a pre-planned path (without collision) from a current location to a target location. The first catheter in a first pose is designated $238_A$ while the first catheter in a second pose is designated $238_B$. Another device in the same general space, for example a second catheter, is shown in a first pose, which is designated $240_A$. FIG. 10 also shows a current location 242 and a target location 244 for the distal tip of the first catheter, which defines a pre-planned path 246. In light of the poses taken by the first catheter 238 relative to the second catheter 240 during the movement along path 245, the collision detection logic 208 will not detect a collision.

Figure 11:
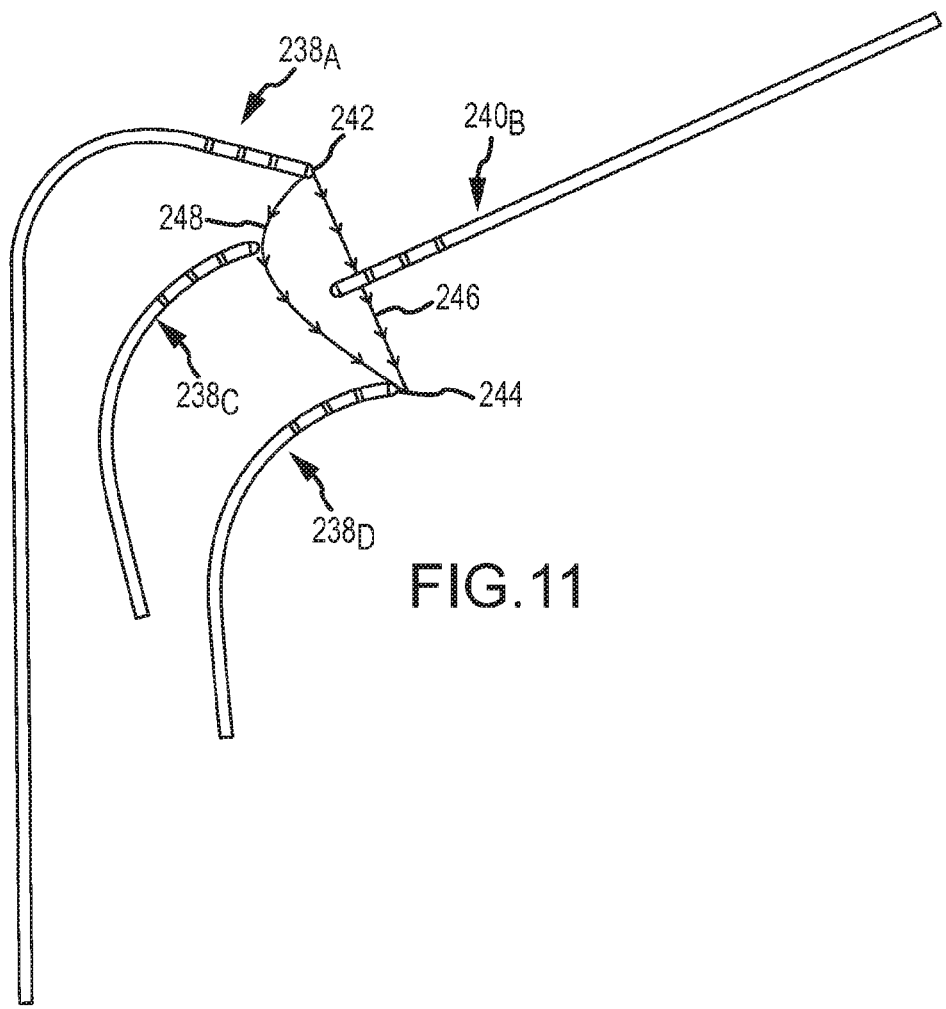
FIG. 11 is a diagrammatic view showing the first and second catheters of FIG. 10 which would result in a collision if the first catheter proceeded along the preplanned path, but which further shows an alternate path that avoids such a collision.

FIG. 11 shows the same two catheters as shown in FIG. 10, but with the second catheter in a second pose designated $240_B$ that is different from the first pose $240_A$ and in fact lies in the pre-planned path 246. The collision detection logic 208 predicts a collision if the first catheter proceeded along the pre-planned path. This collision is reflected in the collision metric 210. In addition the collision detection logic 208 may be further configured in an embodiment to determine the portion of the catheter at which the collision occurred, which information may also be associated with collision metric 210. If the portions of the catheters which experiences the collision are not at the distal tip, the collision may be more critical and may represent an entanglement. However, if the portion on at least one of the catheters is at the distal tip, then the collision may not result in an entanglement, but may rather cause the secondary (non-moving) catheter to lose its position.

As a result, the alternate path determining logic 220, responsive to at least the collision metric 210 indicating future collision, determines an alternate path, designated 248, between current location 242 and target location 244. In this regard, the first catheter is shown in additional, third and fourth poses that are designated $238_C$ and $238_D$, respectively. The new, alternate path 248, including the prospective poses $238_C$ and $238_D$ that would be taken during the movement, avoid a collision between the two catheters.

Addressing Positioning System Inaccuracies.

In the case of a flexible (e.g., catheter) robotic system, the exact position of the manipulated medical device may not be perfectly known. This uncertainty is in contrast to rigid jointed and/or rigid device robotic systems, where uncertainty as to pose is not the norm. With rigid jointed robots, the respective positions of the end effector, each joint, and each segment are generally known with high accuracy. Through the use of positional encoders and the fact that the segments have minimal flexion, the complete pose of such robots (from the base through to the end-effector) can be determined with forward kinematics.

In the case of flexible robots, for example, in the RCGS 10 manipulating a medical device like a catheter, the pose can be highly deformed by forces imposed on the robot (including the catheter/sheath) such as by obstructions or the weight of the workload. This is the exact situation with catheter robotics. Such estimated pose of the catheter can thus be determined imperfectly by forward kinematics or only somewhat better with a navigation system, such as ENSITE NAVX®.

Due to the imperfect estimate of pose, the output of the collision detection logic 208 (unless addressed) could suffer from false positive or false negative detection. It would be desirable to be able to optimize the detection system such that it has high sensitivity and specificity to collision detection. A number of strategies can be taken to attempt to address this. One such strategy would be to adjust the size of the spheres that are used to define the outer surface of the catheter. In the basic case, the radius of the spheres used for detection would match the actual diameter of the catheter. Alternatively, however, the size of the spheres can be increased to exceed that of the actual catheter diameter in order to improve the sensitivity of the algorithm. The sensitivity/selectivity block 218 may therefore be configured to maintain the values for these parameters (e.g., radius of sphere, the number of spheres as described above) and provide such values to collision detection logic 208.

Another strategy would be to provide a fuzzy collision metric (best shown as metric 212b in FIG. 7) that ranges from, for example only, 0% to 100%. This fuzzy collision metric 212b may be in lieu of the Boolean (binary 0 or 1) collision metric 212a. Based on the distance of the closest two spheres respectively selected from the spheres associated with the first and second devices, a partial collision can be determined by collision detection logic 208, even where the spheres are not actually intersecting.

The collision detection logic 208 is configured to execute this interpolation technique, which, as will be described below, generates intermediate poses that can then be used by logic 208 in predicting potential collisions. A challenge with using location data from a catheter navigation system in combination with a spline estimate to predict future poses, is that from time point n to time point (n+1), there is the possibility that the devices (e.g., catheters) might "pass through" each other, even though no collision was detected at either of the specified time points n or (n+1). This problem can manifest itself if there is a long distance between adjacent nodes (e.g., electrodes) in the device and the spline fit between these electrodes obtain different curves (neither of which intersect), even though the position of the nodes of the splines move by a relatively small degree. One way to address this problem is through interpolation.

Figure 12:
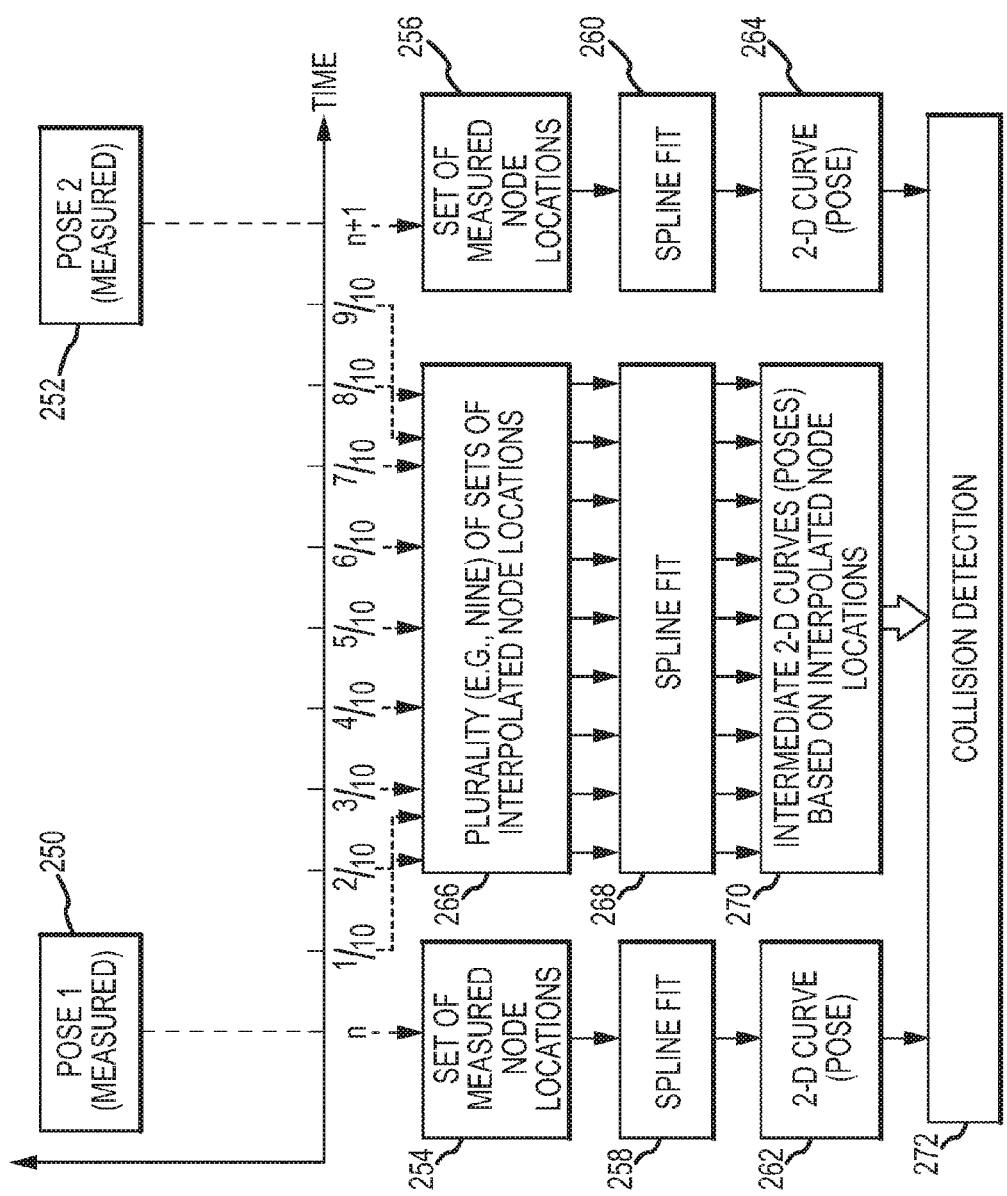
FIG. 12 is a block diagram view of an interpolation scheme for generating intermediate device poses, which are in turn tested for potential collision during a movement of the device.

FIG. 12 is a timing diagram against which are aligned processing blocks of an interpolation technique. As shown in FIG. 12, a first pose (of the device) at time n is represented by block 250 and a second device pose at time (n+1) is represented by block 252. Poses 250 and 252 are based on the measured node locations of the device at times n and (n+1). Such measured node locations are represented by block 254, which corresponds to the measured node locations at time n, and by block 256, which corresponds to the measured node locations at time (n+1). The spline fit function that is applied to the two sets of measured node locations is represented by blocks 258, 260 respectively. The output of the spline fit function blocks 258, 260 results in the device poses at times n and (n+1), represented by block 262 and block 264, respectively. The collision detection logic 208 is configured to use the poses of the device in detecting collision or potential collision of the device with another object (e.g., another device). This is shown in block 272.

The technique performed by collision detection logic 208 involves subdividing the change in the pose of the device between successive time points (i.e., the successive time points being time n and time (n+1) in this example) into a predetermined number of intermediate poses. This subdividing step is based on interpolated node locations. The intermediate poses are then used by logic 208 in the same manner as the poses based on measured node locations (as opposed to interpolated node locations).

With continued reference to FIG. 12, the technique involves sub-dividing the subject time interval into a predetermined number of sub-divisions, which as shown, for example only, as ten (10) sub-divisions or sub-intervals. This is shown on the timeline by fractions $\frac{1}{10}$, $\frac{2}{10}$, $\frac{3}{10}$, etc. The technique further involves computing, for each incremental time sub-division, a respective set of interpolated node locations, using the end points defined by and between the measured node locations. For example only, in FIG. 12, since the time interval between time n and time (n+1) has been sub-divided into ten sub-divisions, nine new sets of interpolated node locations are generated by logic 208, which are collectively represented by block 266. Each new set of interpolated node locations is then subjected to a spline fit function, represented by block 268, to yield a corresponding number of intermediate device splines, from which corresponding poses are determined. The intermediate device poses which are determined are represented by block 270.

Subsequently, logic 208 assesses in block 272 each intermediate device pose with a like-generated device pose for other devices and/or objects. It should be understood that the collision detection comparison (i.e., geometrical solid surface intersection and thus collision) use intermediate poses determined at the same time (time-aligned). The foregoing technique improves the detection capability of collision detection logic 208.

Collision detection logic 208 may be further configured to perform a further technique for determining when splines associated with devices have "passed through" each other. This further technique determines whether a first device (e.g., catheter A) whose pose is determined a later time point (e.g., time n+1) is topologically on the "other side" of a second device (e.g., catheter B) as compared to the pose as determined at a previous time point (e.g., time n). One strategy for performing this technique involves the following steps.

Step (1). The first step involves computing the vector $\vec{w}$ from the center of the closest sphere on catheter A to that on catheter B.

Step (2). The second step involves computing the sign of the dot product of $\vec{w}$ between adjacent time points, in accordance with equation (3) below:

$$s = \text{sign}(\vec{w}_n \cdot \vec{w}_{n-1}) \quad (3)$$

If the sign s is negative, then this is an indication that there is a collision. This technique is suitable if the indices of the closest sphere are the same between adjacent time points or nearly the same. In other words, when the second catheter is stationary or near stationary. In the case where the indices change significantly (i.e., moving), a more sophisticated test to be performed by logic 208 is warranted, as described below.

The more sophisticated test can be accomplished by mapping the device (e.g., catheter) from the real space to a fictitious or virtual space under which each catheter is a straight line segment. This mapping can be accomplished because a spline is homeomorphic with a line segment. A strategy for performing this mapping, using catheter A and catheter B as the exemplary devices, is to consider the two closest spheres, initially at time point n, and involves the following steps.

Step (1). For a sphere on catheter A (i.e., a sphere disposed on a spline for catheter A), constructing a line $\vec{x}$ that passes through the center of this sphere and whose direction coincides with the direction of the spline at that point from proximal to distal.

Step (2). Constructing a vector $\vec{y}$ by performing the same operation as in step (1) for catheter B.

Step (3). Computing the vector $\vec{w}$ from the center of the closest sphere on catheter A to that on catheter B.

Step (4). Using the known electrode spacing, "lay" down a virtual catheter along each line segment such that its position along the line corresponds to the position of its respective closest sphere. This step results in the creation of virtual electrode locations.

Step (5). Associating each sensed electrode location on each catheter to the corresponding virtual electrode location laid down along the line segments in step (4).

Step (6). Computing a mapping from the real, sensed space to a virtual space that corresponds to the space in which the catheters are defined along line segments. The mapping may be expressed as set forth below in equation (4):

$$f:R^3 \to V^3 \qquad (4)$$

The collision detection logic 208 is configured to compute the mapping defined in equation (4) in any suitable manner, such as for example only, either through (i) a thin plate splines algorithm; or (ii) a radial basis function network.

Step (6). Repeating steps (1)-(3) for a subsequent time point (n+1).

Step (7). Transforming the coordinates of the centers of the two closest spheres from time point (n+1) to the virtual space and computing the vector $\vec{u}_{n+1}$ between the two transformed sphere centers.

Step (8). Computing $\vec{u}_n$ which is just $f(\vec{w}_n)$. Since the mapping at this location maps to itself, $\vec{u}_n$ is synonymous with $\vec{w}_n$.

Step (9). Computing the sign of the dot product between $\vec{u}_{n+1}$ and $\vec{w}_n$, which equation is set forth as equation (5) below:

$$s = \text{sign}(\vec{w}_n \cdot \vec{u}_{n+1}) \qquad (5)$$

If the sign s is negative, this outcome is an indication that the catheters have passed through each other and that there has been a collision.

Figure 13:
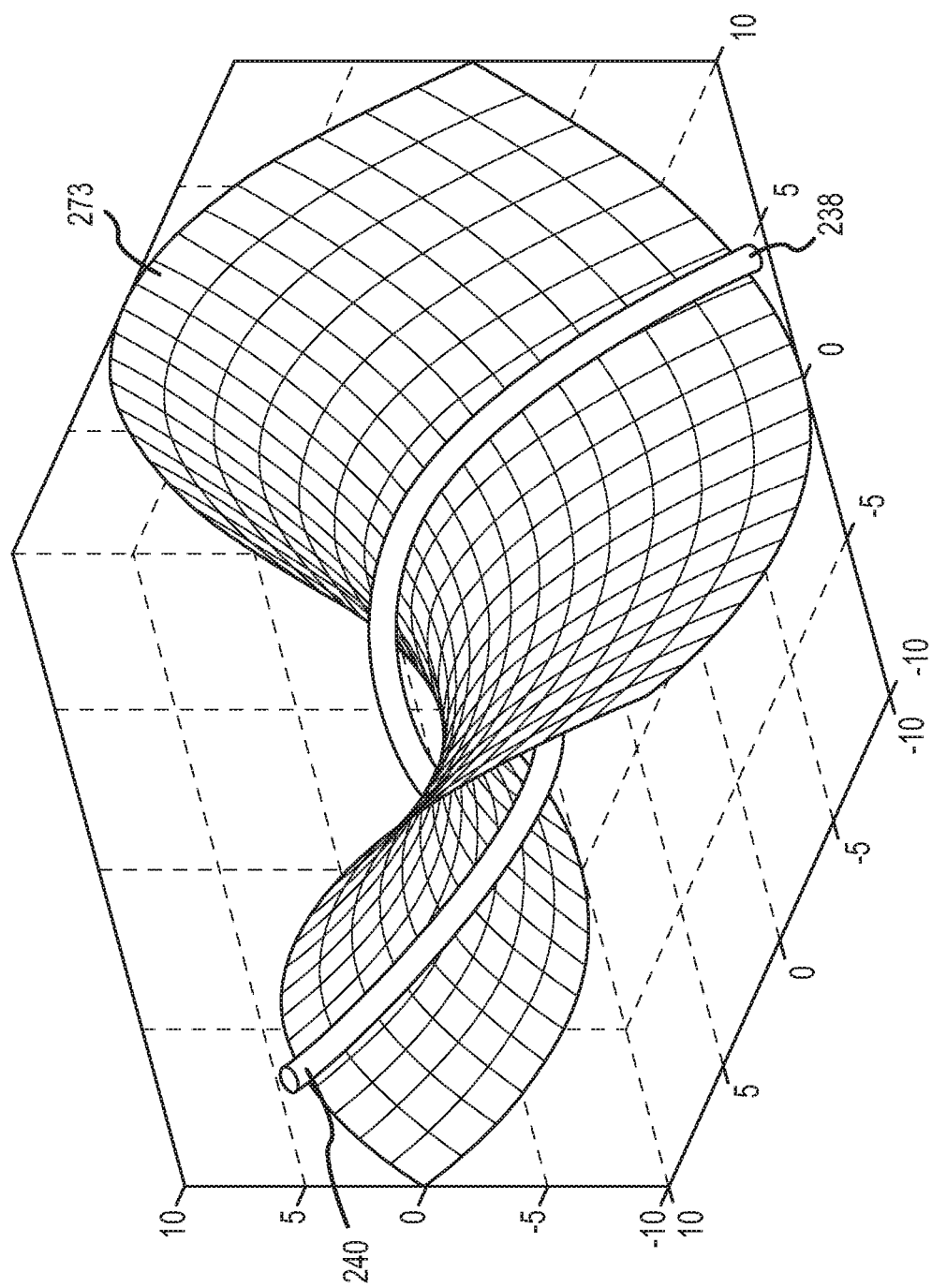
FIG. 13 is an exemplary three-dimensional illustration of a decision boundary surface.

The step (5) above effectively provides a planar surface in the virtual space and acts as a decision boundary, which if the closest spheres crosses, indicates that the catheters have passed through each other. In the real space this decision boundary is a curved surface that separates the two catheters. For example if two catheters are hooked together with opposing 'U' shapes, then the decision boundary in the real space would be a saddle (see FIG. 13, where the two catheters are designated by reference numeral 238, 240 and the decision boundary is designated by reference numeral 273). The mapping of the decision boundary to a planar surface in the virtual space simplifies the process of making the determination, as can be seen in step (9).

Figure 14:
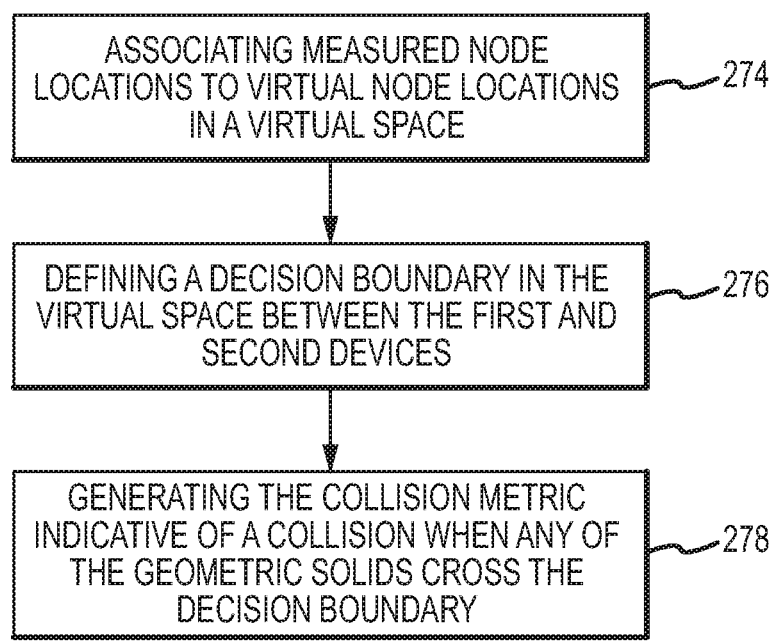
FIG. 14 is a flowchart showing a method of detecting device collisions using a technique involving decision boundary defined in a virtual space.

FIG. 14 is a flowchart of the technique, described above, for detecting when devices have topologically "passed through" each other. The method begins in step 274.

In step 274, the collision detection logic 208 performs the step of associating, for a medical device, the measured node locations with corresponding virtual node locations in a virtual space, where the virtual node locations define line segments, all in the manner described above. The method proceeds to step 276.

In step 276, the logic 208 performs the step of defining a decision boundary in the virtual space between the first and second devices (e.g., catheters). The logic 208 implements this step by performing the sub-step of computing a mapping (e.g., equation (4) above) between the real, sensed space and the virtual space, all as described above. This step may involve logic 208 performing a thin plates spline, using a radial basis function network or using any other algorithm known in the art for such mapping. The method proceeds to step 278.

In step 278, the logic 208 performs the step of generating the collision metric, which is indicative of a collision, when any of the geometrical solids (e.g., spheres) used in simulating the surface(s) of the device(s) cross the decision boundary defined in step 276. This step may be evaluated by computing the sign as set forth in equation (5) above.

A still further method by which the above-described decision boundary can be constructed is through the use of Support Vector Machines (SVM). SVM maps the real space to a higher dimension space where the classes (e.g., here, the catheter A and catheter B electrodes) can be separated by a hyper-plane. The use of a hyper plane reduces the decision calculation to determining on which side of the plane the locations under consideration lie.

Collision Avoidance.

If the direct path of the catheter to its target results in a predicted collision as described above, an alternative path should be planned, which in an embodiment, is performed by alternate path determining logic 220 (best shown in FIG. 7). Logic 220 may be configured to determine an alternate path using a method that involves determine the alternative path in a virtual space defined by the mapping function set forth above in equation (4), namely, $f:R^3 \to V^3$. The virtual space represents a more tractable environment to compute the solution (i.e., the alternate path) since that devices (e.g., catheters) are line segments. Generally, one solution involves determining an alternate path where the moving catheter navigates around the stationary catheter in the virtual space on its trajectory to the target location.

Such a solution can involve forming a line segment in the virtual space that connects the current catheter distal tip to the target location. If the stationary catheter is on one side of this trajectory and the base of the moving catheter is on the opposite side (e.g. the opening of the sheath or the catheter fulcrum), then a collision is likely. A non-colliding trajectory of the moving catheter involves passing on the same side of the stationary catheter as the catheter base. The trajectory may need to be curved in the virtual space to meet these conditions and accomplish a non-colliding movement.

The trajectory can be curved to avoid the stationary catheter in the virtual space by following a trajectory from the current location of the distal tip to the catheter base (by retraction) and then advancing along a straight line defined by the vector from the base to the target. Such a path may be more than is necessary to avoid a collision. A family of curves can be considered that span the alternatives from (i) a straight trajectory to the target to (ii) a 2-step catheter retraction and advancement, substantially in the manner as described. A curve in this family that avoids a collision, but minimizes the need for retraction and advancement would be considered optimal. It should be noted that all of these calculations are with respect to paths in the virtual space, although a heuristic method of simply retracting and advancing the catheter whenever a collision is predicted would work suitably well.

After alternate path determining logic 220 determines a suitable alternate path in the virtual space that avoids a collision, such a path can be transformed back into the real space by applying an inverse transform function, for example as specified in equation (6) below, and which is the inverse function of the mapping function of equation (4):

$$f^{-1} \qquad (6)$$

Once the alternate path has be determined in the real space, the control logic of the RCGS 10 can determine suitable actuation control signals that are operative to move the device (e.g., catheter) to the target location, without collision.

It should be appreciated that numerous variations of the collision detection and avoidance system are possible. For example, it should be understood that while the above examples dealt with two devices, the principles described herein can be easily applied to three or more devices. This can be done by considering the multiplicity of devices on a pair-wise basis. In other words, multiple devices can be considered for collision detection and avoidance purposes by considering all the combinations of devices (e.g., catheters) as pairs. For example, logic 208 may be configured to assess collision detection between three catheter A, B and C by performing individual collision detection assessments between the pairs of A:B, B:C, and C:A. Likewise collision avoidance can be done in the same way. For avoidance, however, the trajectory would need to follow a curve that places all the stationary catheters on an opposite side from the moving catheter's base, which may necessarily require more retraction and advancement.

In addition due to the large number of combinations of geometrical solids (e.g., spheres) that need to be compared, in an embodiment, the system 200 may incorporate a physics engine or GPU (graphical processing unit) accessible to logic 208 so as to facilitate the above-described techniques. Such hardware is particularly suitable due to the parallelizable nature of the comparisons being made.

Moreover, while the RCGS 10 as described herein employed linear actuation, such as by using fingers, slider blocks and the like, the spirit and scope of the disclosures contemplated herein is not so limited and extends to and covers, for example only, a manipulator assembly configured to employ rotary actuation of the control members. In further embodiments, the ECU can be configured to cause the manipulator assembly to either linearly actuate and rotary actuate one or more control members associated with the medical device for at least one of translation, rotation, virtual rotation and deflection movement.

Additional apparatus can be incorporated in or used in connection with the RCGS 10, whether or not illustrated in FIG. 1. For example, the following can be coupled, directly or indirectly, to RCGS 10 or used in connection with RCGS 10, depending on the particular procedure: (1) an electrophysiological monitor or display such as an electrogram signal display; (2) one or more body surface electrodes (skin patches) for application onto the body of a patient (e.g., an RF dispersive indifferent electrode/patch for RF ablation); (3) an irrigation fluid source (gravity feed or pump); and (4) an RF ablation generator (e.g., such as a commercially available unit sold under the model number IBI-1500T RF Cardiac Ablation Generator, available from St. Jude Medical, Inc.). To the extent the medical procedure involves tissue ablation (e.g., cardiac tissue ablation), various types of ablation energy sources (i.e., other than radio-frequency—RF energy) can be used in by a catheter manipulated by RCGS 10, such as ultrasound (e.g. acoustic/ultrasound or HIFU, laser, microwave, cryogenic, chemical, photo-chemical or other energy used (or combinations and/or hybrids thereof) for performing ablative procedures.

As used herein "distal" refers to an end or portion thereof that is advanced to a region of interest within a body (e.g., in the case of a catheter) while "proximal" refers to the end or portion thereof that is opposite of the distal end, and which can be disposed outside of the body and manipulated, for example, automatically through the RCGS 10.

It should be understood that an electronic controller or ECU as described above for certain embodiments can include conventional processing apparatus known in the art, capable of executing pre-programmed instructions stored in an associated memory, all performing in accordance with the functionality described herein. To the extent that the methods described herein are embodied in software, the resulting software can be stored in an associated memory and can also constitute the means for performing such methods. Implementation of certain embodiments, where done so in software, would require no more than routine application of programming skills by one of ordinary skill in the art, in view of the foregoing enabling description. Such an electronic control unit or ECU can further be of the type having both ROM, RAM, a combination of non-volatile and volatile (modifiable) memory so that the software can be stored and yet allow storage and processing of dynamically produced data and/or signals.

It should be further understood that an article of manufacture in accordance with this disclosure includes a computer-readable storage medium having a computer program encoded thereon for implementing the collision detection and avoidance functionality described herein. The computer program includes code to perform one or more of the methods disclosed herein.

Although a number of embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, tight, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the disclosure as defined in the appended claims.

What is claimed is:

1. A method of operating a robotic control system that is configured to manipulate a medical device including one or more nodes and which includes an electronic control unit and a computer-readable memory coupled to the electronic control unit, said method comprising the steps of:

providing, for each of the one or more nodes of the medical device, a respective position sensor configured to produce a respective signal from which respective node locations in a reference coordinate system can be determined;

generating a first virtual representation associated with the medical device using the one or more determined node locations;

generating a second virtual representation associated with an object;

determining, using said control unit, a collision metric indicative of a collision between said medical device and said object based on said virtual representations in accordance with a predetermined detection strategy.

2. The method of claim 1 wherein said medical device is a first catheter and said object is a second catheter, said each of said first and second catheters includes one or more nodes, and wherein said virtual representations of said first and second catheters respectively comprise a first spline and a first plurality of geometrical solids defined along said first spline and a second spline and a second plurality of geometrical solids defined along said second spline, each spline being defined through node locations associated with nodes of the associated catheter, said step of determining said collision metric includes the sub-steps of:

defining first surfaces associated with said first plurality of geometrical solids;

defining second surfaces associated with said second plurality of geometrical solids;

determining whether any portion of said first surfaces intersection any portion of said second surfaces.

3. The method of claim 2 wherein said first and second plurality of geometrical solids comprise spheres, and wherein said step of determining said collision metric includes the sub-step of:

evaluating an expression $(x-y)^2 < (r+s)^2$ which when true is indicative of a collision, and where a first sphere of said first plurality of solids, designated $a_n$, is defined on said first spline and has a center location x in a reference coordinate system and a radius r, and where a second sphere of said second plurality of solids, designated $b_m$, is defined on said second spline and has a center location y in said reference coordinate system and a radius s.

4. The method of claim 2 wherein said step of determining said collision metric includes the further sub-steps of:

determining a space in which a distal portion of said first and second catheters occupy;

partitioning said space into a plurality of cells;

identifying those cells in which the geometrical solids from both said first and second plurality of geometrical solids reside; and evaluating a collision expression only with respect to said identified cells, wherein said collision expression when true is indicative of collision of said catheters.

5. The method of claim 4, wherein said first and second plurality of geometrical solids comprise spheres, and wherein evaluating said collision expression comprises evaluating $(x-y)^2 < (r+s)^2$ which when true is indicative of a collision, and where a first sphere of said first plurality of geometrical solids, designated $a_n$, is defined on said first spline and has a center location x in a reference coordinate system and a radius r, and where a second sphere of said second plurality of geometrical solids, designated $b_m$, is defined on said second spline and has a center location y in said reference coordinate system and a radius s.

6. The method of claim 5 wherein said evaluating said collision expression further comprises providing an adjusted radius sphere so as to provide a corresponding adjustment of a detection sensitivity.

7. The method of claim 2 further comprising:

selecting said position sensor from the group comprising an electrically-conductive electrode, an electromagnetic field sensor, a magnetic resonance imaging tracking coil, a fluoroscopic marker and an ultrasound transducer.

8. The method of claim 2 further comprising:

determining a predicted collision for a path of one of said first and second catheters between a current location and a target location wherein said one catheter is predicted to assume a plurality of poses at a plurality of points in time during movement between said current location and said target location.

9. The method of claim 8 further comprising subdividing adjacent poses defined at adjacent time points by:

determining a plurality of interpolated sets of node location for said one catheter, wherein each set includes interpolated node locations, said interpolated node locations being calculated using respective measured node locations determined at said adjacent time points;

determining a plurality of intermediate splines associated with said one catheter using the interpolated sets of node locations; and determining said collision metric in accordance with poses defined by said intermediate splines.

10. The method of claim 8 wherein said path is an original path, further comprising:

determining an alternate path between said current location and said target location when said collision metric indicates possible collision, said alternate path avoiding said possible collision.

11. The method of claim 2 further comprising:

determining a predicted collision for a path of one of said first and second catheters between a current location and a target location, wherein said node locations are measured node locations;

associating measured node locations that are associated with nodes of said first and second catheters, from a first space to a second, virtual space in which measured node locations become virtual node locations defining respective line segments for each of said first and second catheters;

defining a decision boundary between said first catheter and said second catheter in said second, virtual space by determining a mapping function; and generating said collision metric when any one of said spheres associated with either said first or second catheter cross said decision boundary.

12. The method of claim 1 further comprising selecting said collision metric from one of a Boolean with TRUE or FALSE values and a fuzzy collision parameter with percentage values in the range of 0%-100%.

13. In a robotic control system configured to manipulate a medical device, a method to test for collision between the medical device and an object, comprising the steps of:

(A) measuring a sensor location associated with a node of the medical device;

(B) determining a spline through the measured sensor location to estimate the medical device;

(C) constructing a geometric solid on the spline and around the measured sensor location;

(D) measuring a location of an object; and (E) testing for collision using the constructed geometric solid and the object location.

14. The method of claim 13 wherein step (A) is performed by an electro-anatomical modeling system.

15. The method of claim 13 wherein step (B) includes determining a B-spline.

16. The method of claim 13 wherein the medical device is a first catheter, said spline is a first spline, said sensor location is a first sensor location, and said geometric solid is a first geometric solid, and wherein said object is a second catheter, said method further comprising the steps of:

measuring a second sensor location associated with the second catheter;

determining a second spline through the second sensor location to estimate the second catheter; and constructing a second geometric solid on the second spline and around the second sensor location.

17. The method of claim 16 wherein said step of testing for collision includes determining intersection between said first and second geometric solids.

18. The method of claim 14 wherein said geometric solid comprises spheres and said medical device comprises a catheter, and wherein said electro-anatomical modeling system is configured to display said catheter on a display screen using said spheres.

19. The method of claim 16 wherein said step of testing for collision further includes:

determining a space in which a distal portion of said first and second catheters occupy;

partitioning said space into a plurality of cells;

identifying those cells in which the geometrical solids from both said first and second plurality of geometrical solids reside; and evaluating for collision only with respect to said identified cells.

* * * * *